United States Patent
Daniel et al.

(10) Patent No.: US 9,492,471 B2
(45) Date of Patent: *Nov. 15, 2016

(54) METHODS OF TREATING A DISEASE OR DISORDER ASSOCIATED WITH BRUTON'S TYROSINE KINASE

(71) Applicant: Celgene Avilomics Research, Inc., Bedford, MA (US)

(72) Inventors: Tom Daniel, LaJolla, CA (US); Kenichi Takeshita, New York, NY (US); Kenneth Foon, Summit, NJ (US); Jay Mei, North Wales, PA (US)

(73) Assignee: Celgene Avilomics Research, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/084,190

(22) Filed: Nov. 19, 2013

(65) Prior Publication Data

US 2015/0064173 A1 Mar. 5, 2015

Related U.S. Application Data

(60) Provisional application No. 61/870,720, filed on Aug. 27, 2013.

(51) Int. Cl.

| | | |
|---|---|---|
| *A61K 31/00* | (2006.01) |
| *A61K 31/7076* | (2006.01) |
| *A61K 31/4184* | (2006.01) |
| *A61K 31/505* | (2006.01) |
| *A61K 31/675* | (2006.01) |
| *C07K 16/28* | (2006.01) |
| *A61K 39/395* | (2006.01) |

(52) U.S. Cl.
CPC ........... *A61K 31/7076* (2013.01); *A61K 31/00* (2013.01); *A61K 31/4184* (2013.01); *A61K 31/505* (2013.01); *A61K 31/675* (2013.01); *C07K 16/2887* (2013.01); *A61K 39/395* (2013.01); *A61K 39/39533* (2013.01)

(58) Field of Classification Search
None
See application file for complete search history.

(56) References Cited

U.S. PATENT DOCUMENTS

| | | |
|---|---|---|
| 4,879,303 A | 11/1989 | Davison et al. |
| 5,958,935 A | 9/1999 | Davis et al. |
| 6,093,716 A | 7/2000 | Davis et al. |
| 6,114,333 A | 9/2000 | Davis et al. |
| 6,127,376 A | 10/2000 | Davey et al. |
| 6,160,010 A | 12/2000 | Uckun et al. |
| 6,262,088 B1 | 7/2001 | Phillips |
| 6,469,168 B1 | 10/2002 | Simonek et al. |
| 6,579,983 B1 | 6/2003 | Batchelor et al. |
| 6,593,326 B1 | 7/2003 | Bradbury et al. |
| 6,838,464 B2 | 1/2005 | Pease et al. |
| 6,939,874 B2 | 9/2005 | Harmange et al. |
| 7,060,827 B2 | 6/2006 | Singh et al. |
| 7,122,542 B2 | 10/2006 | Singh et al. |
| 7,125,879 B2 | 10/2006 | Guillemont et al. |
| 7,176,212 B2 | 2/2007 | Breault et al. |
| 7,202,033 B2 | 4/2007 | Prescott et al. |
| 7,241,769 B2 | 7/2007 | Stadtmueller et al. |
| 7,282,504 B2 | 10/2007 | Armistead et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,452,879 B2 | 11/2008 | Singh et al. |
| 7,468,363 B2 | 12/2008 | Zeldis |
| 7,485,724 B2 | 2/2009 | Singh et al. |
| 7,491,732 B2 | 2/2009 | Li et al. |
| 7,498,435 B2 | 3/2009 | Singh et al. |
| 7,504,396 B2 | 3/2009 | Nunes et al. |
| 7,514,444 B2 | 4/2009 | Honigberg et al. |
| 7,514,445 B2 | 4/2009 | Freyne et al. |
| 7,514,446 B2 | 4/2009 | Davis-Ward et al. |
| 7,517,886 B2 | 4/2009 | Singh et al. |
| 7,528,143 B2 | 5/2009 | Noronha et al. |
| 7,531,548 B2 | 5/2009 | Guillemont et al. |
| 7,550,460 B2 | 6/2009 | Singh et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,718,662 B1 | 5/2010 | Chen et al. |
| 7,741,330 B1 | 6/2010 | Chen et al. |
| 7,803,939 B2 | 9/2010 | Singh et al. |

(Continued)

FOREIGN PATENT DOCUMENTS

| | | |
|---|---|---|
| CN | 102558149 A | 7/2012 |
| CN | 103159742 A | 6/2013 |
| EP | 1 054 004 A1 | 11/2000 |
| JP | 07041461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/27825 A1 | 5/2000 |
| WO | WO-00/46203 A2 | 8/2000 |
| WO | WO-00/78731 A1 | 12/2000 |
| WO | WO-01/47897 A1 | 7/2001 |
| WO | WO-01/60816 A1 | 8/2001 |
| WO | WO-01/64654 A1 | 9/2001 |
| WO | WO-01/64655 A1 | 9/2001 |
| WO | WO-01/85699 A2 | 11/2001 |

(Continued)

OTHER PUBLICATIONS

Byers, T. (CA Cancer Journal, 1999, 49: 353-361).*
U.S. Appl. No. 13/518,833, filed Jun. 22, 2012, Gray et al.
U.S. Appl. No. 14/084,201, filed Nov. 19, 2013, Daniel et al.
U.S. Appl. No. 14/084,174, filed Nov. 19, 2013, Daniel et al.
Adeyeye, Moji, Ed., Preformulation in Solid Dosage Form Development, Chapter 2.3, Informa Healthcare, 63-80 (2008).

(Continued)

*Primary Examiner* — Yan Xiao
(74) *Attorney, Agent, or Firm* — Choate, Hall & Stewart, LLP; Kristen C. Buteau

(57) ABSTRACT

The present invention provides methods of treating, stabilizing or lessening the severity or progression of a disease or disorder associated with BTK.

16 Claims, 1 Drawing Sheet

(56) References Cited

U.S. PATENT DOCUMENTS

| | | |
|---|---|---|
| 7,812,029 B1 | 10/2010 | Singh et al. |
| 7,820,819 B2 | 10/2010 | Singh et al. |
| 7,825,116 B2 | 11/2010 | Singh et al. |
| 7,858,633 B2 | 12/2010 | Li et al. |
| 7,879,984 B2 | 2/2011 | Martin et al. |
| 7,884,111 B2 | 2/2011 | Argade et al. |
| 7,906,644 B2 | 3/2011 | Singh et al. |
| 8,088,781 B2 | 1/2012 | Honigberg et al. |
| 8,148,525 B2 | 4/2012 | Singh et al. |
| 8,158,621 B2 | 4/2012 | Singh et al. |
| 8,188,276 B2 | 5/2012 | Singh et al. |
| 8,206,711 B2 | 6/2012 | White et al. |
| 8,334,296 B2 | 12/2012 | Singh et al. |
| 8,338,439 B2 | 12/2012 | Singh et al. |
| 8,450,335 B2 | 5/2013 | Singh et al. |
| 8,501,751 B2 | 8/2013 | Honigberg et al. |
| 8,557,806 B2 | 10/2013 | Singh et al. |
| 8,563,568 B2 | 10/2013 | Witowski et al. |
| 8,609,679 B2 | 12/2013 | Singh et al. |
| 8,710,222 B2 | 4/2014 | Singh et al. |
| 8,735,404 B2 | 5/2014 | Honigberg et al. |
| 8,748,438 B2 | 6/2014 | Honigberg et al. |
| 8,748,597 B2 | 6/2014 | Singh et al. |
| 8,796,255 B2 | 8/2014 | Lee et al. |
| 8,822,685 B2 | 9/2014 | Singh et al. |
| 8,835,430 B2 | 9/2014 | Singh et al. |
| 8,853,397 B2 | 10/2014 | Singh et al. |
| 8,883,435 B2 | 11/2014 | Honigberg et al. |
| 8,883,803 B2 | 11/2014 | Honigberg et al. |
| 8,975,249 B2 | 3/2015 | Lee et al. |
| 9,212,181 B2 | 12/2015 | Singh et al. |
| 9,238,629 B2 | 1/2016 | Lee et al. |
| 9,296,737 B2 | 3/2016 | Singh et al. |
| 9,375,431 B2 | 6/2016 | Lee et al. |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0141143 A1 | 6/2007 | Smithey et al. |
| 2007/0203161 A1 | 8/2007 | Argade et al. |
| 2007/0203162 A1 | 8/2007 | Li et al. |
| 2007/0208034 A1 | 9/2007 | Stadlwieser |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0144330 A1 | 6/2011 | Singh et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1* | 3/2012 | Witowski et al. ............ 514/275 |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0165328 A1 | 6/2012 | Honigberg et al. |
| 2012/0165332 A1 | 6/2012 | Major et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0109709 A1 | 5/2013 | Witowski et al. |
| 2013/0137708 A1 | 5/2013 | Garske et al. |
| 2013/0165462 A1 | 6/2013 | Singh et al. |
| 2013/0195852 A1 | 8/2013 | Buggy et al. |
| 2013/0202611 A1 | 8/2013 | Buggy et al. |
| 2013/0273030 A1 | 10/2013 | Buggy et al. |
| 2014/0057929 A1 | 2/2014 | Witowski et al. |
| 2014/0134265 A1 | 5/2014 | Buggy et al. |
| 2014/0140991 A1 | 5/2014 | Daniel et al. |
| 2014/0142123 A1 | 5/2014 | Honigberg et al. |
| 2014/0142128 A1 | 5/2014 | Daniel et al. |
| 2014/0142129 A1 | 5/2014 | Daniel et al. |
| 2014/0163027 A1 | 6/2014 | Verner et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0303154 A1 | 10/2014 | Singh et al. |
| 2014/0303191 A1 | 10/2014 | Buggy et al. |
| 2014/0330007 A1 | 11/2014 | Singh et al. |

(56) References Cited

U.S. PATENT DOCUMENTS

2014/0371241 A1 12/2014 Buggy et al.
2015/0005297 A1 1/2015 Singh et al.
2015/0025055 A1 1/2015 Lee et al.
2015/0038518 A1 2/2015 Balasubramanian
2015/0064172 A1 3/2015 Daniel et al.
2015/0126504 A1 5/2015 Singh et al.
2015/0139979 A1 5/2015 Daniel et al.
2015/0158823 A1 6/2015 Singh et al.
2015/0246040 A1 9/2015 Lee et al.
2016/0130236 A1 5/2016 Lee et al.

FOREIGN PATENT DOCUMENTS

| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/050068 A1 | 6/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2004/103404 A1 | 12/2004 |
| WO | WO-2005/009443 A1 | 2/2005 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/076706 A1 | 7/2006 |
| WO | WO-2006/078846 A1 | 7/2006 |
| WO | WO-2006/101977 A2 | 9/2006 |
| WO | WO-2006/108487 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/136995 A2 | 11/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/078492 A1 | 6/2012 |
| WO | WO-2012/100459 A1 | 8/2012 |
| WO | WO-2012/135801 A1 | 10/2012 |
| WO | WO-2012/158843 A2 | 11/2012 |
| WO | WO-2013/059738 A2 | 4/2013 |
| WO | WO-2013/063401 A1 | 5/2013 |
| WO | WO-2014/081709 A2 | 5/2014 |
| WO | WO-2014/081712 A2 | 5/2014 |
| WO | WO-2014/081714 A2 | 5/2014 |

OTHER PUBLICATIONS

Adult Non-Hodgkin Lymphoma Treatment (PDQ®), Nat. Can. Inst., retreived Jul. 28, 2014 from web: http://www.cancer.gov/cancertopics/pdg/treatment/adult-non-hodgkins/HealthProfessional/page1.
Advani, R.H. et al., Bruton Tyrosine Kinase Inhibitor Ibrutinib (PCI-32765) Has Significant Activity in Patients With Relapsed/Refractory B-Cell Malignancies, J. Clin. Oncol., pp. 1-9 (2012).
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Badoux, X. et al., A phase II study of lenalidomide as initial treatment of elderly patients with chronic lymphocytic leukemia, Journal of Clinical Oncology, 2010 ASCO Annual Meeting Proceedings, 6508 Oral Abstract Session, 28(15S): 489s (2010).
Balmana et al., BRCA in breast cancer: ESMO Clinical Recommendations, Annals of Oncology, 20(Supplement 4): iv19-iv20 (2009).
Bamborough, P. et al., N-4-Pyrimidinyl-1 H-indazol-4-amine inhibitors of Lck: Indazoles as phenol isosteres with improved pharmacokinetics, Bioorg. & Med. Chem. Lett. 17:4363-4368 (2007).
Bastin, R.J. et al., Salt Selection and Optimisation Procedures for Pharmaceutical New Chemical Entities, Organic Process Research & Development, 4: 427-435, (2000).
Binet, J.L. et al., A New Prognostic Classification of Chronic Lymphocytic Leukemia Derived from a Multivariate Survival Analysis, Cancer, 48: 198-206 (1981).
Buggy, J.J. et al., Bruton tyrosine kinase (BTK) and its role in B-cell malignancy, Int. Rev. Immunol., 31(2): 119-32 (2012).

(56) References Cited

OTHER PUBLICATIONS

Cairo, M. And Bishop, M., Tumourlysis syndrome: new therapeutic strategies and classification, Br. J. Haematol., 127: 3-11 (2004).
Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).
Carter, T. et al, Inhibition of drug-resistant mutants of ABL, KIT, and EGF receptor kinases, Proc. Natl. Acad. Sci. USA 102(31):11011-11016 (2005).
Chanan-Khan, A. et al., Clinical activity of lenalidomide in relapsed or refractory chronic lymphocytic leukemia (CLL) patients: updated results of a phase II clinical trial, Leukemia & Lymphoma, 48(suppl 1): S166 (2007).
Chanan-Khan, A. et al., Clinical Efficacy of Lenalidomide in Patients With Relapsed or Refractory Chronic Lymphocytic Leukemia: Results of a Phase II Study, J. Clin. Oncol., 24: 5343-9 (2006).
Chanan-Khan, A. et al., Results of a phase I clinical trial of thalidomide in combination with fludarabine as initial therapy for patients with treatment-requiring chronic lymphocytic leukemia (CLL), Blood, 106(10): 3348-52 (2005).
Chen, C. et al., A Phase II Study of Lenalidomide in Previously Untreated, Symptomatic Chronic Lymphocytic Leukemia (CLL), American Society of Hematology (ASH) Annual Meeting Abstracts, Part 1, 118(11): Abstract 2042, Session: 232-11 (Dec. 8-11, 2008).
Cheson, B. et al., Report of an International Workshop to Standardize Response Criteria for Non-Hodgkin's Lymphomas, Journal of Clinical Oncology, 17(4): 1244-1253 (1999).
Cockcroft, D.W. and Gault, M.H., Prediction of Creatinine Clearance from Serum Creatinine, Nephron, 16: 31-41 (1976).
Cohen, M. et al., Structural bioinformatics-based design of selective, irreversible inhibitors, Science 308:1318-1321 (2005).
Curto, M. et al., Contact-dependent inhibition of EGFR signaling by Nf2/Merlin, J Cell Biol 177:893-903 (2007).
Dickson, M.A., and Schwartz, G.K., Development of cell-cycle inhibitors for cancer therapy, Current Oncology, 16(2): 36-43 (2009).
Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).
Elder, D.P. et al., The utility of sulfonate salts in drug development, J Pharm Sci., 99(7):2948-61 (2010).
Evans, E. et al.,. Clinical Development of AVL-292; A Potent, Selective Covalent Btk Inhibitor for the Treatment of B Cell Malignancies, Blood (ASH Annual Meeting Abstracts), 118: 3485 (2011).
Eve, H.E. et al.,. Single-agent lenalidomide in relapsed/refractory mantle cell lymphoma: results from a UK phase II study suggest activity and possible gender differences, Br. J. Haematol., 159(2): 154-63 (2012).
Extended European Search Report for EP11816874.9, 5 pages. (Dec. 12, 2014).
Extended European Search Report for EP11838624.2, 5 pages. (Jun. 6, 2014).
Extended European Search Report for EP11838628.3, 7 pages. (Jun. 20, 2014).
Extended European Search Report for EP11839800.7, 8 pages. (Jun. 24, 2014).
Fabian, M. et al., A small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Ferrajoli, A. et al., Lenalidomide induces complete and partial remissions in patients with relapsed and refractory chronic lymphocytic leukemia, Blood, 111(11): 5291-7 (2008).
Fisher, R.I. et al., Comparison of a Standard Regimen (CHOP) with Three Intensive Chemotherapy Regimens for Advanced Non-Hodgkin's Lymphoma, N. Engl. J. Med., 328(14): 1002-1006 (1993).
Fowler, N. et al. The Btk Inhibitor, PCI-32765, Induces Durable Responses with Minimal Toxicity in Patients with Relapsed/Refractory B-Cell Malignancies: Results From a Phase I Study, Blood, 116: Abstract 964 (2010).
Frank, D., STAT signaling in the pathogenesis and treatment of cancer, Mol. Med. 5 :432456 (1999).
Friedberg, J.W. et al., Inhibition of Syk with fostamatinib disodium has significant clinical activity in non-Hodgkin lymphoma and chronic lymphocytic leukemia, Blood, 115(13): 2578-85 (2010).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Galustian, C. et al., Thalidomide-derived immunomodulatory drugs as therapeutic agesnts, Expert. Opin. Biol. Ther., 4(12): 1963-70 (2004).
Ghoneim, K., Synthesis and evaluation of some 2-, 4-, di- substituted -6-methylpyrimidine derivatives for antimicrobial activity, J. Indian Chem. Soc. 63(10):914-917 (1986).
Ghosh, D., 2-4-bis (arylamino) -5- methylpyrimidines as antimicrobial agents, J. Med. Chem. 10(5):974 (1967).
Ghosh, D., 2-4-bis (arylamino) -6-methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Guarini, A. et al., BCR ligation induced by IgM stimulation results in gene expression and functional changes only in IgVH unmutated chronic lymphocytic leukemia (CLL) cells, Blood, 112(3): 782-792 (2008).
Gunnellini, M. and Falchi, L., Therapeutic Activity of Lenalidomide in Mantle Cell Lymphoma and Indolent Non-Hodgkin's Lymphomas, Adv. Hematol., 523842. (2012).
Hainsworth, J.D. et al., Rituximab monoclonal antibody as initial systemic therapy for patients with low-grade non-Hodgkin lymphoma, Blood, 95(10):3052-3056 (2000).
Hallek, M. et al., Addition of rituximab to fludarabine and cyclophosphamide in patients with chronic lymphocytic leukaemia: a randomised, open-label, phase 3 trial, Lancet, 376(9747):1164-1174 (2010).
Hallek, M. et al., Guidelines for the diagnosis and treatment of chronic lymphocytic leukemia: a report from the International Workshop on Chronic Lymphocytic Leukemia updating the National Cancer Institute—Working Group 1996 guidelines, Blood, 111(12):5446-56 (2008).
Harris N.L. et al., Lymphoma classification: from REAL to WHO and beyond. In: DeVita VT, Hellman S, Rosenberg SA, eds. Cancer: Principles and Practice of Oncology Updates. Philadelphia, Pa: Lippincott-Raven, 13(3): 1-14 (1999).
Herman, S.E.M., et al., The Kinase Inhibitor, PCI-32765, Demonstrates Activity in Chronic Lymphocytic Leukemia Cells Independent of Microenvironmental Survival Signals, Blood (ASH Annual Meeting Abstracts), 116: Abstract 1385 (2010).
Hernandez-Ilizaliturri, F.J. et al., Higher response to lenalidomide in relapse/refractory diffuse large B-cell lymphoma in nongerminal center B-cell-like than in germinal center B-cell-phenotype, Cancer, 117(22): 5058-66 (2011).
Hur, W. et al., Clinical stage EGFR inhibitors irreversibly alkylate Bmx kinase, Bioorg. Med. Chem. Lett. 18:5916-5919 (2008).
International Search Report for PCT/US09/48784, 8 pages (Nov. 16, 2009).
International Search Report for PCT/US10/31714, 4 pages (Aug. 13, 2010).
International Search Report for PCT/US10/62432, 4 pages (May 26, 2011).
International Search Report for PCT/US11/46926, 2 pages (Dec. 22, 2011).
International Search Report for PCT/US11/58610, 4 pages (Mar. 27, 2012).

(56) References Cited

OTHER PUBLICATIONS

International Search Report for PCT/US11/58616, 3 pages (Mar. 27, 2012).
International Search Report for PCT/US11/59726, 3 pages (Mar. 20, 2012).
International Search Report for PCT/US12/62133, 2 pages (Dec. 28, 2012).
International Search Report for PCT/US13/70766, 4 pages (Mar. 25, 2014).
International Search Report for PCT/US13/70772, 3 pages (Mar. 25, 2014).
International Search Report for PCT/US13/70776, 4 pages (Mar. 25, 2014).
Irish, J. et al., Altered B-cell receptor signaling kinetics distinguish human follicular lymphoma B cells from tumor-infiltrating nonmalignant B cells, Blood, 108(9): 3135-42 (2006).
Jaffe E.S. And Pittaluga S., Aggressive B-cell lymphomas: a review of new and old entities in the WHO classification, Hematology Am. Soc. Hematol. Educ. Program, 506-14 (2011).
Jemal, A. et al., Cancer statistics, CA Cancer J. Clin., 53(1): 5-26 (2003).
Kataja V. And Castiglione M., Primary breast cancer: ESMO clinical recommendations for diagnosis, treatment and follow-up, Annals of Oncology, 20(Supplement 4): iv10-iv14 (2009).
Kay, NE. The angiogenic status of B-CLL B-Cells: role of the VEGF receptors, Leukemia Res., 28: 221-2 (2004).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Lanasa, M.C., Novel insights into the biology of CLL, Hematology Am. Soc. Hematol. Educ. Program, 70-76 (2010).
Lanham, S. et al., Differential signaling via surface IgM is associated with VH gene mutational status and CD38 expression in chronic lymphocytic leukemia, Blood, 101(3): 1087-1093 (2003).
Li, D. et al., BIBW2992, an irreversible EGFR/HER2 inhibitor highly effective in preclinical lung cancer models, Oncogene 27:4702-4711 (2008).
Lin, N. And Winer, E., New targets for therapy in breast cancer: Small molecule tyrosine kinase inhibitors, Breast Cancer Res 6:204-210 (2004).
Malaviya, R. et al., Targeting Janus Kinase 3 in Mast Cells Prevents Immediate Hypersensitivity Reactions and Anaphylaxis, J. Biol. Chem. 274 :27028-27038 (1999).
McClatchey, A. And Giovannini, M., Membrane organization and tumorigenesis—the NF2 tumor suppressor, Merlin, Genes Dev 19:2265-77 (2005).
McDaniel J.M. et al., Molecular action of lenalidomide in lymphocytes and hematologic malignancies, Adv. Hematol., Article ID 513702, 9 pages (2012).
Merriam-Webster's Online Directory, "Prevent" download on Apr. 7, 2008 from "http//www.merriam-webster.com/dictionary/prevent", p. 1 of 1.
Minkovsky, N. and Berezov, A., BIBW-2992, a dual receptor tyrosine kinase inhibitor for the treatment of solid tumors, Curr Opin Invest Drugs 9:1336-1346 (2008).
Montserrat, E. And Rozman, C., Chronic lymphocytic leukemia: Present status, Ann. Oncol., 6: 219-35 (1995).
Nastoupil, L.J. et al., Diffuse large B-cell lymphoma: current treatment approaches, Oncology, 26(5): 488-95 (2012).
Nelson et al., Screening for breast cancer: an update for the U.S. Preventive Services Task Force, Ann. Intern Med, 151(10): 727-737 (2009).
Pelton, P. et al., Ruffling membrane, stress fiber, cell spreading and proliferation abnormalities in human Schwann cells, Oncogene 17:2195-2209 (1998).
Ponader, S. et al., Bruton's Tyrosine Kinase Inhibitor PCI-32765 Abrogates BCR-and Nurselike Cell-Derived Activation of CLL Cells In Vitroand In Vivo, Blood, 116(21): 11 (2010).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Rai, K.R., A critical analysis of staging in CLL, Chronic Lymphocytic Leukemia: Recent Progress and Future Directions, 253-264 (1987).
Readinger, J. et al., Selective Targeting of ITK Blocks Multiple Steps of HIV Replication, Proc. Natl. Acad. Sci. USA 105: 6684-6689 (2008).
Rinaldi, A. et al., Genomic and expression profiling identifies the B-cell associated tyrosine kinase Syk as a possible therapeutic target in mantle cell lymphoma, Br. J. Haematol., 132(3): 303-16 (2006).
Ruiz-Ballesteros, E. et al., Splenic marginal zone lymphoma: proposal of new diagnostic and prognostic markers identified after tissue and cDNA microarray analysis. Blood, 106(5): 1831-8 (2005).
Schlessingerman, Mass of an Adult Male, The Physics Factbook (2003), retreived Jul. 22, 2014 from web: http://hypertextbook.com/facts/2003/AlexSchleesingerman.shtml.
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Steinhardt, J.J. And Gartenhaus, R.B., Promising Personalized Therapeutic Options for Diffuse Large B-cell Lymphoma Subtypes with Oncogene Addictions, Clin. Cancer Res., 18(17): 4538-4548 (2012).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Supplementary European Search Report for EP10844293.0, 8 pages (Jun. 27, 2013).
Tohnya, T.M. et al., A phase I study of oral CC-5013 (lenalidomide, Revlimid), a thalidomide derivative, in patients with refractory metastatic cancer, Clin Prostate Cancer, 2(4): 241-3 (2004).
Trieu, V. et al., A specific inhibitor of janus kinase-3 increases survival in a transgenic mouse model of amyotrophic lateral sclerosis, Biochem. Biophys. Res. Commun. 267 :22-25 (2000).
US Department of Health and Human Services Food and Drug Administration Guidance for; Industry Drug-Induced Liver Injury: Premarketing Clinical Evaluation. Available from: URL:; http://www.fda.gov/downloads/Drugs/GuidanceComplianceRegulatoryInformation/Guidances/U; CM174090.pdf (accessed Jul. 25, 2012).
Wiernik, P.H. et al., Lenalidomide monotherapy in relapsed or refractory aggressive non-Hodgkin's lymphoma, J. Clin. Oncol., 26(30): 4952-7 (2008).
Winer, E.S. et al., A novel Bruton's tyrosine kinase inhibitor for the treatment of lymphoid malignancies, Expert Opin. Investig. Drugs, 21(3): 355-61 (2012).
Witzig, T.E. et al., Lenalidomide oral monotherapy produces durable responses in relapsed or refractory indolent non-Hodgkin's Lymphoma, J. Clin. Oncol., 27(32): 5404-5409 (2009).
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (Nov. 16, 2009).
Written Opinion for PCT/US10/31714, 8 pages (Aug. 13, 2010).

(56) References Cited

OTHER PUBLICATIONS

Written Opinion for PCT/US10/62432, 14 pages (May 26, 2011).
Written Opinion for PCT/US11/46926, 9 pages (Dec. 22, 2011).
Written Opinion for PCT/US11/58610, 8 pages (Mar. 27, 2012).
Written Opinion for PCT/US11/58616, 9 pages (Mar. 27, 2012).
Written Opinion for PCT/US11/59726, 7 pages (Mar. 20, 2012).
Written Opinion for PCT/US12/62133, 11 pages (Dec. 28, 2012).
Written Opinion for PCT/US13/70766, 11 pages (Mar. 25, 2014).
Written Opinion for PCT/US13/70772, 10 pages (Mar. 25, 2014).
Written Opinion for PCT/US13/70776, 11 pages (Mar. 25, 2014).
Yang, H.T. et al., Coordinate Regulation of TPL-2 and NF-kB Signaling in Macrophages by NF kB1, Mol. Cell. Biol., 32(17): 3438-51 (2012).
Yang, Y. et al., Exploiting Synthetic Lethality for the Therapy of ABC Diffuse Large B Cell Lymphoma, Cancer Cell, 21: 723-737 (2012).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
Zhu, D. et al., Immunomodulatory drugs Revlimid (lenalidomide) and CC-4047 induce apoptosis of both hematological and solid tumor cells through NK cell activation. Cancer Immunol. Immunother., 57(12): 1849-59 (2008).
U.S. Appl. No. 14/636,905, filed Mar. 3, 2015, Lee et al.
Brown, J.R. et al., Phase Ib trial of AVL-292, a covalent inhibitor of Bruton's tyrosine kinase (Btk), in chronic lymphocytic leukemia (CLL) and B-non-Hodgkin lymphoma (B-NHL), 2012 ASCO Annual Meeting, J. Clin. Oncol., 30 (suppl; abstr 8032): 1-2 pages (2012).
Chronic Lymphocytic Leukemia/Small Lymphocytic Lymphoma (CLL/SLL), Lymphoma Research Foundation, www.lymphoma.org, pp. 1-4, Apr. 21, 2015.
Gunnellini, M. And Falchi, L., Therapeutic Activity of Lenalidomide in Mantle Cell Lymphoma and Indolent Non-Hodgkin's Lymphomas, Adv. Hematol., 523842: 7 pages (2012).
Kiesewetter, B. et al., A phase II study of lenalidomide in patients with extranodal marginal zone B-cell lymphoma of the mucosa associated lymphoid tissue (MALT-lymphoma), Haematologica, 98(3): 353-356 (2012).
Leonard, J. et al., A randomized trial of lenalidomide alone versus lenalidomide plus rituximab in patients with recurrent follicular lymphoma, 2012 ASCO Anual Meeting, J. Clin. Oncol., 30 (suppl; abstr 8000): 1-2 pages (2012).
Olejniczak, S.H. et al., Acquired Resistance to Rituximab Is Associated with Chemotherapy Resistance Resulting from Decreased Bax and Bak Expression, Clinical Cancer Research, 14(5):1550-1560 (2008).
Rituxan Prescribing Information, http://www.gene.com/download/pdf/rituxan_prescribing.pdf, Genetech USA, Inc. Aug. 2014.
Smith, M.R. et al, Rituximab (monoclonal anti-CD20 antibody): mechanisms of action and resistance, Oncogene, 22:7359-7368 (2003).
Tsai, P-C et al., Regulation of CD20 in Rituximab-Resistant Cell Lines and B-cell Non-Hodgkin Lymphoma, Clinical Cancer Research, 18(4):1039-1050 (2012).
Westlin, W. et al., Translational medicine enables rapid early clinical development of AVL-292, a highly selective, orally available inhibitor of Bruton's tyrosine kinase, in a phase 1b clinical trial, Cancer Res., 72(8) Supplement 1: 1-2 pages (2012).
Yang, Y. et al., Exploiting Synthetic Lethality for the Therapy of ABC Diffuse Large B Cell Lymphoma, Cancer Cell, 21: 723-737 (2012). Supplemental Information S1.

Zhang, L. et al., Synergistic antitumor effects of lenalidomide and rituximab on mantle cell lymphoma in vitro and in vitro, American Journal of Hematology, 84: 553-559 (2009).
Adult Non-Hodgkin Lymphoma Treatment (PDQ®), Nat. Can. Inst., retrieved Jul. 28, 2014 from web: http://www.cancer.gov/cancertopics/pdg/treatment/adult-non-hodgkins/HealthProfessional/page1.
O'Brien, S. et al., The Bruton's Tyrosine Kinase (BTK) Inhibitor PCI-32765 Induces Durable Responses in Relapsed or Refractory (R/R) Chronic Lymphocytic Leukemia/Small Lymphocytic Lymphoma (CLL/SLL): Follow-up of a Phase Ib/II Study, Blood (ASH Annual Meeting Abstracts), 118: Abstract 983 (2011).
Sjin, R. et al., In vitro and in vivo characterization of irreversible mutant-selective EGFR inhibitors that are wild-type sparing, Molecular Cancer Therapeutics, 13(6):1468-1479 (2014).
U.S. Appl. No. 15/080,351, filed Mar. 24, 2016, Singh et al.
Author Not Known, Chemotherapeutic options in chronic lymphocytic leukemia: a meta-analysis of the randomized trials. CLL Trialists' Collaborative Group, J. Natl. Cancer Inst., 91(10): 861-868 (1999).
Burger, J.A. et al., The Btk Inhibitor Ibrutinib (PCI-32765) in Combination with Rituximab is well Tolerated and Displays Profound Activity in High-Risk Chronic Lymphocytic Leukemia (CLL) Patients, 54th ASH Annual Meeting and Exposition, American Society of Hematology, Abstract 187: 4 pages (Dec. 9, 2012). URL: https://ash.confex.com/ash/2012/webprogram/Paper47509.html [Retrieved Feb. 12, 2015].
Damle, R.N. et al., Abstract 3531: Changes in immune cell populations in relapsed/refractory CLL patients treated with a Bruton's Tyrosine Kinase (BTK) Inhibitor, Ibrutinib (PCI-32765), in combination with Bendamustine and Rituximab (BR), Cancer Research, Proceedings: AACR 104th Annual Meeting 2013, 73(Abstract 3531): 3 pages (Apr. 15, 2013). URL: http://cancerres.aacrjournals.org/content/73/8_Supplement/3531.short [Retrieved Feb. 17, 2015].
European Search Report for EP13856559.3, 8 pages. (May 10, 2016).
European Search Report for EP13857254.0, 8 pages. (May 11, 2016).
Kilo, M.N. And Dorfman, D.M., The Utility of Flow Cytometric Immunophenotypic Analysis in the Distinction of Small Lymphocytic Lymphoma/Chronic Lymphocytic Leukemia From Mantle Cell Lymphoma, Am. J. Clin. Pathol., 105(4): 451-457 (1996).
Kim, A.S., Clinical Impact og Gene Expression Profiling on Oncology Diagnosis, Prognosis, and Treatment, Combinatorial Chemistry & High Throughout Screening, 7: 183-206 (2004).
Ludovici, D. W. et al., Evolution of anti-HIV drug candidates. Part 3: Diarylpyrimidine (DAPY) analogues, Bioorganic & Medicinal Chemistry Letters, 11(17): 2235-2239 (2001).
Molot, R.J. et al., Antigen Expression and Polymerase Chain Reaction Amplification of Mantle Cell Lymphoma, Blood, 83(6): 1626-1631 (1994).
Mordant, C. et al., Synthesis of novel diarylpyrimidine analogues of TMC278 and their antiviral activity against HIV-1 wild-type and mutant strains, Eur. J. Med. Chem., 42(5): 567-579 (2006).
Rebehmed, J. et al., 2D and 3D QSAR studies of diarylpyrimidine HIV-1 reverse transcriptase inhibitors, Journal of Computer-Aided Molecular Design, 22(11): 831-841 (2008).
Thakur, A. et al., SAR and QSAR studies: Modelling of new DAPY derivatives, European Journal of Medicinal Chemistry, 43(3): 471-477 (2008).
Yatabe, Y. et al., Significance of cyclin D1 overexpression for the diagnosis of mantle cell lymphoma: a clinicopathologic comparison of cyclin D1-positive MCL and cyclin D1-negative MCL-like B-cell lymphoma, Blood, 95(7): 2253-2261 (2000).

* cited by examiner

Response Assessments of Patients in Cohorts 1 and 2

| PATIENT | Cohort | Cycle 1 | Cycle 2 | Cycle 3 | Cycle 4 | Cycle 5 | Cycle 7 |
|---|---|---|---|---|---|---|---|
| A | 1 | NA | PR | PR | PR | PR | PR |
| B | 1 | NA | PR | PR | PR | PR | PR |
| C | 1 | NA | PR | PR | NA | PR | PR |
| A | 2 | NA | PR | - | - | - | - |
| B | 2 | NA | PR | - | - | - | - |
| C | 2 | NA | PR | - | - | - | - |

NA: not available
PR: partial response

METHODS OF TREATING A DISEASE OR DISORDER ASSOCIATED WITH BRUTON'S TYROSINE KINASE

CROSS REFERENCE TO RELATED APPLICATIONS

The present application claims priority to U.S. provisional application No. 61/870,720, filed Aug. 27, 2013, the entirety of which is hereby incorporated by reference.

FIELD OF THE INVENTION

The present invention provides methods of treating, stabilizing or lessening the severity or progression of a disease or disorder associated with Bruton's Tyrosine Kinase ("BTK").

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

Accordingly, there remains a need to find protein kinase inhibitors useful as therapeutic agents.

SUMMARY OF THE INVENTION

Chronic lymphocytic leukemia (CLL) is a lymphoproliferative malignancy characterized by progressive accumulation of morphologically mature but functionally incompetent lymphocytes in the blood, bone marrow, and lymphoid tissues. It affects mainly elderly individuals with the median age at presentation of 65 to 70 years. Small lymphocytic lymphoma (SLL) and CLL are generally considered a different manifestation of the same disease. While CLL is found in the blood and bone marrow, SLL presents primarily in the lymph nodes. The clinical course of CLL/SLL ranges from indolent disease with long-term survival over 12 years to aggressive disease with median survival of 2 years. The average age of diagnosis with CLL/SLL is approximately 60 years.

Despite newly approved therapeutic agents and combination therapies, CLL/SLL remains an incurable disease and most patients eventually relapse and/or die. Improved and novel combination treatments for subjects with CLL/SLL requiring treatment remain an unmet medical need.

Bruton's tyrosine kinase (Btk) is a non-receptor tyrosine kinase with restricted cellular expression largely limited to B-lymphocytes, monocytes, and mast cells or basophils. Btk is a critical component of the B-cell receptor (BCR) signaling network and is crucial for B-cell development. Investigation has revealed that some B-cell malignancies, including diseases such as CLL/SLL, depend on BCR signaling, suggesting that interruption of such signaling could be a promising therapeutic opportunity. Recently, clinical anti-tumor responses in various B-cell non-Hodgkin's Lymphoma (NHL) and CLL/SLL have been reported with agents that inhibit spleen tyrosine kinase (Syk) and Btk, both components of the BCR signaling pathway.

United States published patent application number US 2010/0029610, published Feb. 4, 2010 ("the '610 publication," the entirety of which is hereby incorporated herein by reference), describes certain 2,4-disubstituted pyrimidine compounds which covalently and irreversibly inhibit activity of one or more protein kinases, including BTK, a member of TEC-kinases. Such compounds include N-(3-(5-fluoro-2-(4-(2-methoxyethoxy)phenylamino)pyrimidin-4-ylamino) phenyl)acrylamide, hereinafter referred to as Compound 1, which is designated as compound number 1-182 in the '610 publication. The synthesis of Compound 1 is described in detail at Example 20 of the '610 publication Compound 1 is active in a variety of assays and therapeutic models demonstrating covalent, irreversible inhibition of BTK (in enzymatic and cellular assays). Notably, Compound 1 is a potent, selective, orally available, small molecule which was found to inhibit B-cell proliferation and activation. Compound 1 is therefore useful for treating one or more disorders associated with activity of BTK.

Accordingly, among other things, the present invention provides methods of treating, stabilizing or lessening the severity or progression of one or more diseases and conditions associated with BTK. In some aspects, the present invention provides methods of treating, stabilizing or lessening the severity or progression of one or more diseases and conditions associated with BTK comprising administering to a patient in need thereof a pharmaceutically acceptable composition comprising N-(3-(5-fluoro-2-(4-(2-methoxyethoxy)phenylamino)pyrimidin-4-ylamino)phenyl)acrylamide (1):

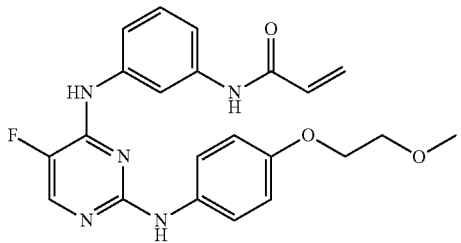

In some embodiments, the present invention provides a method of treating, stabilizing or lessening the severity or progression of one or more diseases and conditions associated with BTK comprising administering to a patient in need thereof Compound 1 in combination with rituximab.

In some embodiments, the present invention provides a method of treating, stabilizing or lessening the severity or progression of one or more diseases and conditions associated with BTK comprising administering to a patient in need thereof a composition comprising Compound 1 in combination with a composition comprising rituximab.

In some embodiments, provided methods comprise administering to a patient in need thereof Compound 1 in combination with rituximab, wherein Compound 1 is administered once a day. In some embodiments, provided methods comprise administering to a patient in need thereof Compound 1 in combination with rituximab, wherein Compound 1 is administered twice a day. In some such embodiments, rituximab is administered once during a 28-day cycle. Accordingly, in some embodiments, provided methods comprise administering to a patient in need thereof Compound 1 in combination with rituximab, wherein Compound 1 is administered twice a day and rituximab is administered once during a 28-day cycle.

In some embodiments, the provided methods comprise administering to a patient in need thereof a composition comprising Compound 1 and rituximab.

In some embodiments, the provided methods comprise administering to a patient in need thereof Compound 1, rituximab, fludarabine and cyclophosphamide.

In some embodiments, the provided methods comprise administering to a patient in need thereof Compound 1, rituximab and bendamustine.

In some embodiments, the disease or condition associated with BTK is selected from chronic lymphocytic leukemia and small lymphocytic lymphoma.

In some embodiments, the present invention provides a method of treating, stabilizing or lessening the severity or progression of chronic lymphocytic leukemia (CLL), the method comprising administering to a patient in need thereof Compound 1 in combination with rituximab.

In some embodiments, the present invention provides a method of treating, stabilizing or lessening the severity or progression of small lymphocytic lymphoma (SLL), the method comprising administering to a patient in need thereof Compound 1 in combination with rituximab.

In some embodiments, provided therapies comprise orally administering to a patient Compound 1 in combination with rituximab. In some embodiments, each of Compound 1 and rituximab is administered in the form of a pharmaceutical formulation. In some embodiments, the pharmaceutical formulation comprising Compound 1 is a capsule formulation. In some embodiments, the pharmaceutical formulation comprising rituximab is an intravenous (IV) formulation.

In some embodiments, the present invention also provides dosing regimens and protocols for administering to patients in need thereof Compound 1 in combination with rituximab. Such methods, dosing regimens and protocols for the administration of said combination are described in further detail, below.

BRIEF DESCRIPTION OF THE DRAWINGS

FIG. 1 presents the Response Assessments of patients enrolled in cohorts 1 and 2 as of Oct. 16, 2013.

DETAILED DESCRIPTION OF THE INVENTION

Definitions

As used herein, the term "antibody", or grammatical variations thereof (i.e., antibodies), refers to polypeptide(s) capable of binding to an epitope. In some embodiments, an antibody is a full-length antibody. In some embodiments, an antibody is less than full length (i.e., an antibody fragment) but includes at least one binding site. In some such embodiments, the binding site comprises at least one, and preferably at least two sequences with structure of antibody variable regions. In some embodiments, the term "antibody" encompasses any protein having a binding domain which is homologous or largely homologous to an immunoglobulin-binding domain. In particular embodiments, the term "antibody" encompasses polypeptides having a binding domain that shows at least 99% identity with an immunoglobulin-binding domain. In some embodiments, the antibody is any protein having a binding domain that shows at least 70%, at least 80%, at least 85%, at least 90% or at least 95% identity with an immunoglobulin-binding domain. Antibody polypeptides in accordance with the present invention may be prepared by any available means, including, for example, isolation from a natural source or antibody library, recombinant production in or with a host system, chemical synthesis, etc., or combinations thereof. In some embodiments, an antibody is monoclonal or polyclonal. In some embodiments, an antibody may be a member of any immunoglobulin class, including any of the human classes IgG, IgM, IgA, IgD and IgE. In certain embodiments, an antibody is a member of the IgG immunoglobulin class. In some embodiments, the term "antibody" refers to any derivative of an antibody that possesses the ability to bind to an epitope of interest. In some embodiments, an antibody fragment comprises multiple chains that are linked together, for example, by disulfide linkages. In some embodiments, an antibody is a human antibody. In some embodiments, an antibody is a humanized antibody. In some embodiments, humanized antibodies include chimeric immunoglobulins, immunoglobulin chains or antibody fragments (Fv, Fab, Fab', F(ab')$_2$ or other antigen binding subsequences of antibodies) that contain minimal sequence derived from non-human immunoglobulin. In some embodiments, humanized antibodies are human immunoglobulin (recipient antibody) in which residues from a complementary-determining region (CDR) of the recipient are replaced by residues from a CDR of a non-human species (donor antibody) such as mouse, rat or rabbit having the desired specificity, affinity and capacity. In particular embodiments, antibodies for use in the present invention bind to particular epitopes of CD20. In some embodiments, epitopes of CD20 to which anti-CD20 antibodies bind include, for example, $^{170}$ANPS$^{173}$ (Binder et al., *Blood* 2006, 108(6): 1975-1978), FMC7 (Deans et al., *Blood* 2008, 111(4): 2492), Rp5-L and Rp15-C (mimotopes of CD20) (Perosa et al., *J. Immunol.* 2009, 182:416-423), $^{182}$YCYSI$^{185}$ (Binder et al., *Blood* 2006, 108(6): 1975-1978) and WEWTI (a mimic of $^{182}$YCYSI$^{185}$) (Binder et al., *Blood* 2006, 108(6): 1975-1978). In some embodiments, an anti-CD20 antibody has a binding affinity ($K_d$) for an epitope of CD20 of less than 12 nM, less than 11 nM, less than 10 nM, less than 9 nM, less than 8 nM, less than 7 nM, less than 6 nM, less than 5 nM, less than 4 nM, less than 3 nM, less than 2 nM or less than 1 nM.

As used herein, the term "biosimilar" (for example, of an approved reference product/biological drug, such as a protein therapeutic, antibody, etc.) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is approved and intended to be used and for which approval is sought (e.g., that there are no clinically meaningful differences between the biological product and the reference product in terms of the safety, purity, and potency of the product).

In some embodiments, the biosimilar biological product and reference product utilizes the same mechanism or mechanisms of action for the condition or conditions of use prescribed, recommended, or suggested in the proposed labeling, but only to the extent the mechanism or mechanisms of action are known for the reference product. In some embodiments, the condition or conditions of use prescribed, recommended, or suggested in the labeling proposed for the biological product have been previously approved for the reference product. In some embodiments, the route of administration, the dosage form, and/or the strength of the biological product are the same as those of the reference product. In some embodiments, the facility in which the biological product is manufactured, processed, packed, or held meets standards designed to assure that the biological product continues to be safe, pure, and potent. The reference product may be approved in at least one of the U.S., Europe, or Japan. A biosimilar can be for example, a presently known antibody having the same primary amino acid sequence as a marketed antibody, but may be made in different cell types or by different production, purification or formulation methods.

As used herein, the terms "combination", "in combination with" or "combination therapy" refer to those situations in which two or more different pharmaceutical agents are administered in overlapping regimens so that the subject is simultaneously exposed to both agents. In some embodiments, such combinations refer to simultaneously administering to a subject separate dosage forms of Compound 1 and rituximab. In some embodiments, such combinations refer to contemporaneously administering to a subject separate dosage forms of Compound 1 and rituximab, wherein Compound 1 is administered before, during or after administration of rituximab. In some embodiments, simultaneous or contemporaneous exposure of Compound 1 and rituximab is effected via different dosage regimens appropriate for each therapeutic agent. For example, Compound 1 may be administered once or twice daily for one or more 28-day cycles, whereas rituximab may be administered once during a 28-day cycle.

The term "percent inhibition" as used herein refers to the percent decrease of target activity in the presence of a test compound (e.g., an irreversible BTK inhibitor) relative to control target activity. It will be appreciated that percent inhibition of a target (e.g., a kinase) can be determined in numerous ways, one of which is described in Example 2, infra. In some embodiments, percent inhibition is expressed as % inhibition (e.g., 50% inhibition). In some embodiments, the percent inhibition of a kinase is an average percent inhibition.

As used herein, the term "comparable", refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable. As used herein, the terms "comparable percent inhibition" or "comparable average percent inhibition" refer to a percent inhibition or an average percent inhibition, respectively, of a kinase that is within 10% of that observed or determined for a reference kinase inhibitor. For example, if a reference kinase inhibitor has 50% inhibition of a kinase relative to a control, another inhibitor will be considered to show comparable inhibition if it has about 40% to about 60% inhibition of the same kinase relative to the control. In some embodiments, an irreversible BTK inhibitor has comparable percent inhibition to a reference kinase inhibitor wherein the percent inhibition of the irreversible BTK inhibitor is within 9%, 8%, 7%, 6%, 5%, 4%, 3%, 2% or 1% inhibition of that observed or determined for a reference kinase inhibitor.

As used herein, a "disease or disorder associated with BTK" or a "BTK-mediated disorder" means any disease or other deleterious condition in which BTK, or a mutant thereof, is known or suspected to play a role. Accordingly, another embodiment of the present invention relates to preventing, treating, stabilizing or lessening the severity or progression of one or more diseases in which BTK, or a mutant thereof, is known or suspected to play a role. Specifically, the present invention relates to a method of treating or lessening the severity of a proliferative disorder, wherein said method comprises administering to a patient in need thereof Compound 1 in combination with rituximab.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

The term "refractory CLL/SLL" as used herein is defined as CLL/SLL which was treated with at least one line of prior therapy (i) without achieving at least a partial response to therapy or (ii) which progressed within 6 months of treatment.

The term "relapsed CLL/SLL" as used herein is defined as CLL/SLL which progressed after ≥6 months post-treatment after achieving partial response or complete response to therapy.

The term "subject", as used herein, means a mammal and includes human and animal subjects, such as domestic animals (e.g., horses, dogs, cats, etc.).

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disorder or condition associated with Bruton's tyrosine kinase.

The terms "treat" or "treating," as used herein, refers to partially or completely alleviating, inhibiting, delaying onset of, preventing, ameliorating and/or relieving a disorder or condition, or one or more symptoms of the disorder or condition. As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

The expression "unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

General Methods of Treating a BTK-Mediated Disease or Disorder

In some embodiments, the present invention provides a method of treating, stabilizing or lessening the severity or progression of one or more diseases and conditions associated with BTK comprising administering to a patient in need thereof an irreversible BTK inhibitor and rituximab. In some such embodiments, provided methods further comprise administering fludarabine and cyclophosphamide.

It is understood that although the methods described herein refer to formulations, doses and dosing regimens/schedules of Compound 1 and salts thereof, such formulatiosn, doses and/or dosing regimens/schedules are equally applicable to any irreversible BTK inhibitor, such as those described below. Accordingly, in some embodiments, a dose or dosing regimen of an irreversible BTK inhibitor is selected from any of the doses or dosing regimens for Compound 1 as described herein. In some embodiments, provided methods comprise administering an irreversible BTK inhibitor in an amount selected from any of the doses for Compound 1 as described herein. In some such embodiments, a dose of an irreversible BTK inhibitor is administered according to a dosing schedule selected from any of the dosing schedules described herein for Compound 1. In some embodiments, a composition comprising an irreversible BTK inhibitor is any of the formulations as described herein.

In some embodiments, the present invention provides a method of treating, stabilizing or lessening the severity or progression of one or more diseases and conditions associated with BTK comprising administering to a patient in need thereof an irreversible BTK inhibitor and rituximab and bendamustine.

In some embodiments, the irreversible BTK inhibitor covalently binds to Cys 481 of BTK.

In some embodiments, an irreversible BTK inhibitor has activity against one or more kinases selected from the kinases recited in Table 3, infra.

In some embodiments, an irreversible BTK inhibitor has a percent inhibition comparable to that of a reference kinase inhibitor with respect to a kinase selected from Table 3, or combinations thereof. In some such embodiments, the reference kinase inhibitor is Compound 2:

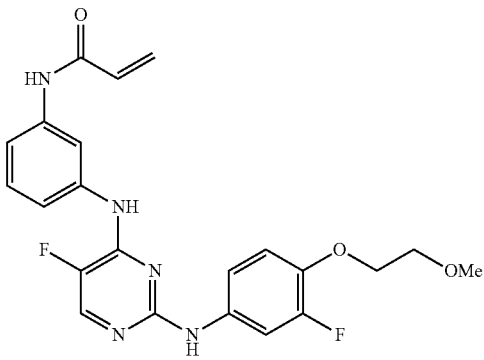

Compound 2

In some embodiments, the percent inhibition of the reference kinase inhibitor is that shown for Compound 2 in Example 2.

In some embodiments, an irreversible BTK inhibitor has a percent inhibition comparable to that of Compound 2 with respect to one or more kinases selected from Table 3, or combinations thereof, in that the irreversible kinase inhibitor has a percent inhibition within approximately 10% of that observed for Compound 2. In some embodiments, an irreversible BTK inhibitor has a percent inhibition comparable to that of Compound 2 with respect to one or more kinases selected from Table 3, or combinations thereof, in that the irreversible kinase inhibitor has a percent inhibition that is within about 9%, or about 8%, or about 7%, or about 6%, or about 5%, or about 4%, or about 3%, or about 2% or about 1% inhibition of that observed for Compound 2.

In some embodiments, an irreversible BTK inhibitor has a percent inhibition that is greater than that observed for Compound 2 with respect to one or more kinases selected from Table 3. In some embodiments, an irreversible BTK inhibitor has a percent inhibition that is less than that observed for Compound 2 with respect to one or more kinases selected from Table 3.

In some embodiments, the irreversible BTK inhibitor has a percent inhibition of one or more additional kinases, wherein the percent inhibition of the kinase or kinases is at least about 50%, at least about 55%, at least about 60%, at least about 65%, at least about 70%, at least about 75%, at least about 80%, at least about 85%, at least about 90% or at least about 95%.

In some embodiments, the irreversible BTK inhibitor has a percent inhibition comparable to that of a reference kinase inhibitor with respect to one or more kinases selected from the group consisting of TXK, BMX/ETK, FLT3, BLK, TEC, ERBB4/HER4, Aurora B, TRKC, RET, LOK/STK10, Aurora C, FLT4/VEGFR3, ROS/ROS1, ARK5/NUAK1, EGFR, DDR1, JAK3, LRRK2, ABL2/ARG, ITK, Aurora A, YES/YES1, FGFR3, TNK1, BRK, FGFR2, PDGFRb, c-SRC, ACK1, FGFR1, STK16, ABL1, AXL, TYK2, ERBB2/HER2, FGR, CHK2, SIK1, MLK1/MAP3K9, MLK2/MAP3K10, MLK3/MAP3K11, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition comparable to that of a reference kinase inhibitor with respect to the group of kinases consisting of TXK, BMX/ETK, FLT3, BLK, TEC, ERBB4/HER4, Aurora B, TRKC, RET, LOK/STK10, Aurora C, FLT4/VEGFR3, ROS/ROS1, ARK5/NUAK1, EGFR, DDR1, JAK3, LRRK2, ABL2/ARG, ITK, Aurora A, YES/YES1, FGFR3, TNK1, BRK, FGFR2, PDGFRb, c-SRC, ACK1, FGFR1, STK16, ABL1, AXL, TYK2, ERBB2/HER2, FGR, CHK2, SIK1, MLK1/MAP3K9, MLK2/MAP3K10, MLK3/MAP3K11, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor inhibits a kinase selected from the group consisting of TXK, BMX/ETK, FLT3, BLK, TEC, ERBB4/HER4, Aurora B, TRKC, RET, LOK/STK10, Aurora C, FLT4/VEGFR3, ROS/ROS1, ARK5/NUAK1, EGFR, DDR1, JAK3, LRRK2, ABL2/ARG, ITK, Aurora A, YES/YES1, FGFR3, TNK1, BRK, FGFR2, PDGFRb, c-SRC, ACK1, FGFR1, STK16, ABL1, AXL, TYK2, ERBB2/HER2, FGR, CHK2, SIK1, MLK1/MAP3K9, MLK2/MAP3K10, MLK3/MAP3K11, PKCb2 and CLK2, or combinations thereof, wherein the inhibition of the kinase or kinases is at least the percent inhibition observed for a reference kinase inhibitor. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has at least about 50%, at least about 55%, at least about 60%, at least 65%, at least about 70%, at least about 75%, at least about 80%, at least about 85%, at least about 90% or at least about 95% inhibition of a kinase selected from TXK, BMX/ETK, FLT3, BLK, TEC, ERBB4/HER4, Aurora B, TRKC, RET, LOK/STK10, Aurora C, FLT4/VEGFR3, ROS/ROS1, ARK5/NUAK1, EGFR, DDR1, JAK3, LRRK2, ABL2/ARG, ITK, Aurora A, YES/YES1, FGFR3, TNK1, BRK, FGFR2, PDGFRb, c-SRC, ACK1, FGFR1, STK16, ABL1, AXL, TYK2, ERBB2/HER2, FGR, CHK2, SIK1, MLK1/MAP3K9, MLK2/MAP3K10, MLK3/MAP3K11, PKCb2 and CLK2, or combinations thereof.

In some embodiments, the irreversible BTK inhibitor has a percent inhibition comparable to that of a reference kinase inhibitor with respect to one or more kinases selected from the group consisting of Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition comparable to that of a reference kinase inhibitor with respect to the group of kinases consisting of Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition that is at least the percent inhibition observed for a reference kinase inhibitor with respect to one or more kinases selected from the group consisting of Aurora A, Aurora B, Aurora C, TRKC, ROS/ROS1, ARK5/

NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has at least about 50%, at least about 55%, at least about 60%, at least about 65%, at least about 70%, at least about 75%, at least about 80%, at least about 85%, at least about 90% or at least about 95% inhibition of a kinase selected from Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2, or combinations thereof.

In some embodiments, the present invention provides a method of treating, stabilizing or lessening the severity or progression of CLL/SLL comprising administering to a patient in need thereof an irreversible BTK inhibitor in combination with rituximab, wherein the irreversible BTK inhibitor has not more than about 50% inhibition of a kinase selected from Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2, or combinations thereof.

In some embodiments, the irreversible BTK inhibitor has at least about 50% inhibition of a kinase selected from Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11 and PKCb2, or combinations thereof. In some embodiments, the irreversible BTK inhibitor has has at least about 50% inhibition of the group of kinases consisting of Aurora A, Aurora B, Aurora C, TRKC, ROS/ROS1, ARK5/NUAK1, LRRK2, ABL2/ARG, TNK1, STK16, ABL1, AXL, TYK2, CHK2, SIK1, MLK1/MAP3K9, MLK2/MAP3K10, MLK3/MAP3K11, PKCb2 and CLK2.

In some embodiments, the irreversible BTK inhibitor has at least about 55% inhibition of a kinase selected from Aurora A, Aurora B, Aurora C, TRKC, ROS/ROS1, ARK5/NUAK1, LRRK2, ABL2/ARG, TNK1, STK16, ABL1, CHK2, MLK1/MAP3K9, MLK2/MAP3K10 and MLK3/MAP3K11, or combinations thereof. In some embodiments, the irreversible BTK inhibitor has at least about 55% inhibition of the group of kinases consisting of Aurora A, Aurora B, Aurora C, TRKC, ROS/ROS1, ARK5/NUAK1, LRRK2, ABL2/ARG, TNK1, STK16, ABL1, CHK2, MLK1/MAP3K9, MLK2/MAP3K10 and MLK3/MAP3K11.

In some embodiments, the irreversible BTK inhibitor has at least about 60% inhibition of a kinase selected from Aurora A, Aurora B, Aurora C, TRKC, ROS/ROS1, ARK5/NUAK1, LRRK2, ABL2/ARG, TNK1, STK16, CHK2, MLK1/MAP3K9 and MLK3/MAP3K11, or combinations thereof. In some embodiments, the irreversible BTK inhibitor has at least about 60% inhibition of the group of kinases consisting of Aurora A, Aurora B, Aurora C, TRKC, ROS/ROS1, ARK5/NUAK1, LRRK2, ABL2/ARG, TNK1, STK16, CHK2, MLK1/MAP3K9 and MLK3/MAP3K11.

In some embodiments, the irreversible BTK inhibitor has at least about 65% inhibition of a kinase selected from Aurora A, Aurora B, Aurora C, TRKC, ROS/ROS1, ARK5/NUAK1, LRRK2, TNK1, STK16, CHK2, MLK1/MAP3K9 and MLK3/MAP3K11, or combinations thereof. In some embodiments, the irreversible BTK inhibitor sh at least about 65% inhibition of the group of kinases consisting of Aurora A, Aurora B, Aurora C, TRKC, ROS/ROS1, ARK5/NUAK1, LRRK2, TNK1, STK16, CHK2, MLK1/MAP3K9 and MLK3/MAP3K11.

In some embodiments, the irreversible BTK inhibitor has at least about 70% inhibition of a kinase selected from Aurora A, Aurora B, Aurora C, ROS/ROS1, ARK5/NUAK1, TNK1, STK16, CHK2, MLK1/MAP3K9 and MLK3/MAP3K11, or combinations thereof. In some embodiments, the irreversible BTK inhibitor at least about 70% inhibition of the group of kinases consisting of Aurora A, Aurora B, Aurora C, ROS/ROS1, ARK5/NUAK1, TNK1, STK16, CHK2, MLK1/MAP3K9 and MLK3/MAP3K11.

In some embodiments, the irreversible BTK inhibitor has at least about 75% inhibition of a kinase selected from Aurora A, Aurora B, ROS/ROS1, ARK5/NUAK1, TNK1, STK16 and MLK1/MAP3K9, or combinations thereof. In some embodiments, the irreversible BTK inhibitor has at least about 75% inhibition of the group of kinases consisting of Aurora A, Aurora B, ROS/ROS1, ARK5/NUAK1, TNK1, STK16 and MLK1/MAP3K9.

In some embodiments, the irreversible BTK inhibitor has at least about 80% inhibition of a kinase selected from Aurora A, Aurora B, ROS/ROS1, ARK5/NUAK1, TNK1 and MLK1/MAP3K9, or combinations thereof. In some embodiments, the irreversible BTK inhibitor has at least about 80% inhibition of the group of kinases consisting of Aurora A, Aurora B, ROS/ROS1, ARK5/NUAK1, TNK1 and MLK1/MAP3K9.

In some embodiments, the irreversible BTK inhibitor has at least about 85% inhibition of a kinase selected from Aurora A, Aurora B, ROS/ROS1, ARK5/NUAK1 and MLK1/MAP3K9, or combinations thereof. In some embodiments, the irreversible BTK inhibitor has at least about 85% inhibition of the group of kinases consisting of Aurora A, Aurora B, ROS/ROS1, ARK5/NUAK1 and MLK1/MAP3K9.

In some embodiments, the irreversible BTK inhibitor has a percent inhibition comparable to that of a reference kinase inhibitor with respect to one or more kinases selected from the group consisting of TNK1, STK16, ABL1, AXL, TYK2, CHK2, MLK1/MAP3K9, MLK2/MAP3K10, MLK3/MAP3K11, SIK1, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition comparable to that of a reference kinase inhibitor with respect to the group of kinases consisting of TNK1, STK16, ABL1, AXL, TYK2, CHK2, MLK1/MAP3K9, MLK2/MAP3K10, MLK3/MAP3K11, SIK1, PKCb2 and CLK2, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition that is at least the percent inhibition observed for a reference kinase inhibitor with respect to one or more kinases selected from the group consisting of TNK1, STK16, ABL1, AXL, TYK2, CHK2, MLK1/MAP3K9, MLK2/MAP3K10, MLK3/MAP3K11, SIK1, PKCb2 and CLK2, or combinations thereof. In some embodiments, the reference kinase inhibitor is Compound 2.

In some embodiments, the percent inhibition of the reference kinase inhibitor is that shown for Compound 2 in Example 2.

In some embodiments, the irreversible BTK inhibitor has at least about 50%, at least about 55%, at least about 60%, at least about 65%, at least about 70%, at least about 75%, at least about 80%, at least about 85%, at least about 90% or at least about 95% inhibition of a kinase selected from TNK1, STK16, ABL1, AXL, TYK2, CHK2, MLK1/MAP3K9, MLK2/MAP3K10, MLK3/MAP3K11, SIK1, PKCb2 and CLK2, or combinations thereof.

In some embodiments, the irreversible BTK inhibitor has at least about 50% inhibition of a kinase selected from TNK1, STK16, ABL1, AXL, TYK2, CHK2, MLK1/MAP3K9, MLK2/MAP3K10, MLK3/MAP3K11, SIK1, PKCb2 and CLK2, or combinations thereof. In some embodiments, the irreversible BTK inhibitor at least about 50% inhibition of the group of kinases consisting of TNK1, STK16, ABL1, AXL, TYK2, CHK2, MLK1/MAP3K9, MLK2/MAP3K10, MLK3/MAP3K11, SIK1, PKCb2 and CLK2.

In some embodiments, the irreversible BTK inhibitor has at least about 55% inhibition of a kinase selected from TNK1, STK16, ABL1, CHK2, MLK1/MAP3K9 and MLK3/MAP3K11, or combinations thereof. In some embodiments, the irreversible BTK inhibitor has at least about 55% inhibition of the group of kinases consisting of TNK1, STK16, ABL1, CHK2, MLK1/MAP3K9 and MLK3/MAP3K11, or combinations thereof.

In some embodiments, the irreversible BTK inhibitor has at least about 60%, at least about 65% or at least about 70% inhibition of a kinase selected from TNK1, STK16, CHK2, MLK1/MAP3K9 and MLK3/MAP3K11, or combinations thereof. In some embodiments, the irreversible BTK inhibitor has at least about 60%, at least about 65% or at least about 70% inhibition of the group of kinases consisting of CHK2, MLK1/MAP3K9 and MLK3/MAP3K11.

In some embodiments, the irreversible BTK inhibitor has at least about 75% inhibition of a kinase selected from TNK1, STK16 and MLK1/MAP3K9, or combinations thereof. In some embodiments, the irreversible BTK inhibitor has at least about 75% inhibition of the group of kinases consisting of TNK1, STK16 and MLK1/MAP3K9.

In some embodiments, an irreversible BTK inhibitor for use in the present invention has a percent inhibition comparable to that of a reference kinase inhibitor with respect to one or more kinases selected from the group consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition comparable to that of a reference kinase inhibitor with respect to the group of kinases consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition that is not more than the percent inhibition observed for a reference kinase inhibitor with respect to one or more kinases selected from the group consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has not more than about 50%, not more than about 45%, not more than about 40%, not more than about 35%, not more than about 30%, not more than about 25%, not more than about 20%, not more than about 15%, not more than about 10% or not more than about 5% inhibition of a kinase selected from c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof.

In some embodiments, the irreversible BTK inhibitor has not more than about 50%, not more than about 45%, not more than about 40%, not more than about 35%, not more than about 30%, not more than about 25%, not more than about 20%, not more than about 15%, not more than about 10% or not more than about 5% inhibition of a kinase selected from RIPK2, HCK, LYN, CSK, LCK, LYN B and FYN, or combinations thereof.

In some embodiments, the irreversible BTK inhibitor has not more than about 50%, not more than about 45%, not more than about 40%, not more than about 35%, not more than about 30%, not more than about 25%, not more than about 20%, not more than about 15%, not more than about 10% or not more than about 5% inhibition of a kinase selected from EPHA6, LYN B, FRK/PTK5, RIPK3, BRAF, ARAF and SRMS, or combinations thereof.

In some embodiments, the present invention provides a method of treating, stabilizing or lessening the severity or progression of CLL/SLL comprising administering to a patient in need thereof an irreversible BTK inhibitor in combination with rituximab, wherein the irreversible BTK inhibitor has at least about 50% inhibition of a kinase selected from c-Kit, PDGFRa, RIPK2, HCK, EPHA6, LYN, CSK, LCK, ZAK/MLTK, LYN B, FRK/PTK5, FYN, BRAF, RIPK3, ARAF and SRMS, or combinations thereof.

In some embodiments, the irreversible BTK inhibitor has not more than about 50% inhibition of a kinase selected from c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the irreversible BTK inhibitor has not more than about 50% inhibition of the group of kinases consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS.

In some embodiments, the irreversible BTK inhibitor has not more than about 45% inhibition of a kinase selected from c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the irreversible BTK inhibitor has not more than about 45% inhibition of the group of kinases consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS.

In some embodiments, the irreversible BTK inhibitor has not more than about 40% inhibition of a kinase selected from c-Kit, PDGFRa, RIPK2, HCK, EPHA6, LYN, CSK, LCK, ZAK/MLTK, LYN B, FRK/PTK5, FYN, RIPK3, BRAF, ARAF and SRMS, or combinations thereof. In some embodiments, the irreversible BTK inhibitor has not more than about 40% inhibition of the group of kinases consisting of c-Kit, PDGFRa, RIPK2, HCK, EPHA6, LYN, CSK, LCK, ZAK/MLTK, LYN B, FRK/PTK5, FYN, RIPK3, BRAF, ARAF and SRMS.

In some embodiments, the irreversible BTK inhibitor has not more than about 35% inhibition of a kinase selected from c-Kit, RIPK2, HCK, EPHA6, LYN, CSK, ZAK/MLTK, LYN B, FRK/PTK5, FYN, RIPK3, BRAF, ARAF and SRMS, or combinations thereof. In some embodiments, the irreversible BTK inhibitor has not more than about 35% inhibition of the group of kinases consisting of c-Kit, RIPK2, HCK, EPHA6, LYN, CSK, ZAK/MLTK, LYN B, FRK/PTK5, FYN, RIPK3, BRAF, ARAF and SRMS.

In some embodiments, the irreversible BTK inhibitor has not more than about 30% inhibition of a kinase selected from c-Kit, RIPK2, HCK, EPHA6, LYN, CSK, ZAK/MLTK, LYN B, FRK/PTK5, FYN, RIPK3, BRAF, ARAF and SRMS, or combinations thereof. In some embodiments, the irreversible BTK inhibitor has not more than about 30% inhibition of the group of kinases consisting of c-Kit, RIPK2, HCK, EPHA6, LYN, CSK, ZAK/MLTK, LYN B, FRK/PTK5, FYN, RIPK3, BRAF, ARAF and SRMS.

In some embodiments, the irreversible BTK inhibitor has not more than about 25% inhibition of a kinase selected from c-Kit, RIPK2, EPHA6, CSK, ZAK/MLTK, LYN B, FRK/PTK5, FYN, RIPK3, BRAF, ARAF and SRMS, or combinations thereof. In some embodiments, the irreversible BTK inhibitor has not more than about 25% inhibition of the group of kinases consisting of c-Kit, IPK2, EPHA6, CSK, ZAK/MLTK, LYN B, FRK/PTK5, FYN, RIPK3, BRAF, ARAF and SRMS.

In some embodiments, the irreversible BTK inhibitor has not more than about 20% inhibition of a kinase selected from EPHA6, CSK, ZAK/MLTK, LYN B, FRK/PTK5, FYN, RIPK3, BRAF, ARAF and SRMS, or combinations thereof. In some embodiments, the irreversible BTK inhibitor has not more than about 20% inhibition of the group of kinases consisting of EPHA6, CSK, ZAK/MLTK, LYN B, FRK/PTK5, FYN, RIPK3, BRAF, ARAF and SRMS.

In some embodiments, the irreversible BTK inhibitor has not more than about 15% inhibition of a kinase selected from EPHA6, LYN B, FRK/PTK5, RIPK3, BRAF, ARAF and SRMS, or combinations thereof. In some embodiments, the irreversible BTK inhibitor has not more than about 15% inhibition of the group of kinases consisting of EPHA6, LYN B, FRK/PTK5, RIPK3, BRAF, ARAF and SRMS.

In some embodiments, the irreversible BTK inhibitor has not more than about 10% inhibition of a kinase selected from EPHA6, LYN B, FRK/PTK5, RIPK3, BRAF, ARAF and SRMS, or combinations thereof. In some embodiments, the irreversible BTK inhibitor has not more than about 10% inhibition of the group of kinases consisting of EPHA6, LYN B, FRK/PTK5, RIPK3, BRAF, ARAF and SRMS.

In some embodiments, the irreversible BTK inhibitor has not more than about 5% inhibition of a kinase selected from EPHA6, FRK/PTK5, RIPK3, BRAF, ARAF and SRMS, or combinations thereof. In some embodiments, the irreversible BTK inhibitor has not more than about 5% inhibition of the group of kinases consisting of EPHA6, FRK/PTK5, RIPK3, BRAF, ARAF and SRMS.

In some embodiments, the irreversible BTK inhibitor has a percent inhibition of LYN comparable to that of a reference kinase inhibitor. In some embodiments, the irreversible BTK inhibitor has a percent inhibition of LYN that is not more than that observed for a reference kinase inhibitor. In some embodiments, the irreversible BTK inhibitor has a percent inhibition of LYN that is about 20-30%. In some embodiments, the irreversible BTK inhibitor has a percent inhibition of LYN that is about 25-30%. In some embodiments, the irreversible BTK inhibitor has a percent inhibition of LYN that is about 25-28%. In some embodiments, the irreversible BTK inhibitor has a percent inhibition of LYN that is not more than about 25%, not more than about 26%, not more than about 27%, not more than about 28%, not more than about 29%, not more than about 30%, not more than about 31%, not more than about 32% or not more than about 33%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of c-Kit comparable to that of a reference kinase inhibitor. In some embodiments, the irreversible BTK inhibitor has a percent inhibition of c-Kit that is not more than that observed for a reference kinase inhibitor. In some embodiments, the irreversible BTK inhibitor has a percent inhibition of c-Kit that is about 15-25%. In some embodiments, the irreversible BTK inhibitor has a percent inhibition of c-Kit that is about 20-25%. In some embodiments, the irreversible BTK inhibitor has a percent inhibition of c-Kit that is about 20-23%. In some embodiments, the irreversible BTK inhibitor has a percent inhibition of c-Kit that is not more than about 15%, not more than about 16%, not more than about 17%, not more than about 18%, not more than about 19%, not more than about 20%, not more than about 21%, not more than about 22%, not more than about 23%, not more than about 24% or not more than about 25%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of PDGFRa comparable to that of a reference kinase inhibitor. In some embodiments, the irreversible BTK inhibitor has a percent inhibition of PDGFRa that is not more than that observed for a reference kinase inhibitor. In some embodiments, the irreversible BTK inhibitor has a percent inhibition of PDGFRa that is about 30-40%. In some embodiments, the irreversible BTK inhibitor has a percent inhibition of PDGFRa that is about 35-40%. In some embodiments, the irreversible BTK inhibitor has a percent inhibition of PDGFRa that is about 35-38%. In some embodiments, the irreversible BTK inhibitor has a percent inhibition of PDGFRa that is not more than about 30%, not more than about 31%, not more than about 32%, not more than about 33%, not more than about 34%, not more than about 35%, not more than about 36%, not more than about 37%, not more than about 38%, not more than about 39% or not more than about 40%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of RIPK2 comparable to that of a reference kinase inhibitor. In some embodiments, the irreversible BTK inhibitor has a percent inhibition of RIPK2 that is not more than that observed for a reference kinase inhibitor. In some embodiments, the irreversible BTK inhibitor has a percent inhibition of RIPK2 that is about 20-30%. In some embodiments, the irreversible BTK inhibitor has a percent inhibition of RIPK2 that is about 20-25%. In some embodiments, the irreversible BTK inhibitor has a percent inhibition of RIPK2 that is about 22-25%. In some embodiments, the irreversible BTK inhibitor has a percent inhibition of RIPK2 that is not more than about 18%, not more than about 19%, not more than about 20%, not more than about 21%, not more than about 22%, not more than about 23%, not more than about 24%, not more than about 25%, not more than about 26% or not more than about 27%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of HCK comparable to that of a reference kinase inhibitor. In some embodiments, the irreversible BTK inhibitor has a percent inhibition of HCK that is not more than that observed for a reference kinase inhibitor. In some embodiments, the irreversible BTK inhibitor has a percent inhibition of HCK that is about 25-35%. In some embodiments, the irreversible BTK inhibitor has a percent inhibition of HCK that is about 27-32%. In some embodiments, the irreversible BTK inhibitor has a percent inhibition of HCK that is about 28-31%. In some embodiments, the irreversible BTK inhibitor has a percent inhibition of HCK that is not more than about 26%, not more than about 27%, not more than about 28%, not more than about 29%, not more than about 30%, not more than about 31%, not more than about 32%, not more than about 33% or not more than about 34%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of EPHA6 comparable to that of a reference kinase inhibitor. In some embodiments, the irreversible BTK inhibitor has a percent inhibition of EPHA6 that is not more than that observed for a reference kinase inhibitor. In some embodiments, the irreversible BTK inhibitor has a percent inhibition of EPHA6 that is about 0-10%. In some embodiments, the irreversible BTK inhibitor has a percent inhibition of EPHA6 that is about 0-5%. In some embodiments, the irreversible BTK inhibitor has a percent inhibition of EPHA6 that is about 0-3%. In some embodiments, the irreversible BTK inhibitor has a percent inhibition of EPHA6 that is not more than about 0.5%, not more than about 0.6%, not more than about 0.7%, not more than about 0.8%, not more than about 0.9%, not more than about 1%, not more than about 2%, not more than about 3% or not more than about 4%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of CSK comparable to that of a reference kinase inhibitor. In some embodiments, the irreversible BTK inhibitor has a percent inhibition of CSK that is not more than that observed for a reference kinase inhibitor. In some embodiments, the irreversible BTK inhibitor has a percent inhibition of CSK that is about 10-20%. In some embodiments, the irreversible BTK inhibitor has a percent inhibition of CSK that is about 15-20%. In some embodiments, the irreversible BTK inhibitor has a percent inhibition of CSK that is about 16-19%. In some embodiments, the irreversible BTK inhibitor has a percent inhibition of CSK that is not more than about 15%, not more than about 16%, not more than about 17%, not more than about 18%, not more than about 19%, not more than about 20%, not more than about 21%, not more than about 22% or not more than about 23%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of LCK comparable to that of a reference kinase inhibitor. In some embodiments, the irreversible BTK inhibitor has a percent inhibition of LCK that is not more than that observed for a reference kinase inhibitor. In some embodiments, the irreversible BTK inhibitor has a percent inhibition of LCK that is about 30-40%. In some embodiments, the irreversible BTK inhibitor has a percent inhibition of LCK that is about 32-37%. In some embodiments, the irreversible BTK inhibitor has a percent inhibition of LCK that is about 34-37%. In some embodiments, the irreversible BTK inhibitor has a percent inhibition of LCK that is not more than about 34%, not more than about 35%, not more than about 36%, not more than about 37%, not more than about 38%, not more than about 39%, not more than about 40%, not more than about 41% or not more than about 42%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of ZAK/MLTK comparable to that of a reference kinase inhibitor. In some embodiments, the irreversible BTK inhibitor has a percent inhibition of ZAK/MLTK that is not more than that observed for a reference kinase inhibitor. In some embodiments, the irreversible BTK inhibitor has a percent inhibition of ZAK/MLTK that is about 10-20%. In some embodiments, the irreversible BTK inhibitor has a percent inhibition of ZAK/MLTK that is about 12-17%. In some embodiments, the irreversible BTK inhibitor has a percent inhibition of ZAK/MLTK that is about 14-17%. In some embodiments, the irreversible BTK inhibitor has a percent inhibition of ZAK/MLTK that is not more than about 12%, not more than about 13%, not more than about 14%, not more than about 15%, not more than about 16%, not more than about 17%, not more than about 18%, not more than about 19% or not more than about 20%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of LYN B comparable to that of a reference kinase inhibitor. In some embodiments, the irreversible BTK inhibitor has a percent inhibition of LYN B that is not more than that observed for a reference kinase inhibitor. In some embodiments, the irreversible BTK inhibitor has a percent inhibition of LYN B that is about 0-10%. In some embodiments, the irreversible BTK inhibitor has a percent inhibition of LYN B that is about 3-8%. In some embodiments, the irreversible BTK inhibitor has a percent inhibition of LYN B that is about 4-7%. In some embodiments, the irreversible BTK inhibitor has a percent inhibition of LYN B that is not more than about 1%, not more than about 2%, not more than about 3%, not more than about 4%, not more than about 5%, not more than about 6%, not more than about 7%, not more than about 8%, not more than about 9% or not more than about 10%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of FRK/PTK5 comparable to that of a reference kinase inhibitor. In some embodiments, the irreversible BTK inhibitor has a percent inhibition of FRK/PTK5 that is not more than that observed for a reference kinase inhibitor. In some embodiments, the irreversible BTK inhibitor has a percent inhibition of FRK/PTK5 that is about 0-10%. In some embodiments, the irreversible BTK inhibitor has a percent inhibition of FRK/PTK5 that is about 0-5%. In some embodiments, the irreversible BTK inhibitor has a percent inhibition of FRK/PTK5 that is about 0-3%. In some embodiments, the irreversible BTK inhibitor has a percent inhibition of FRK/PTK5 that is not more than about 0.5%, not more than about 0.6%, not more than about 0.7%, not more than about 0.8%, not more than about 0.9%, not more than about 1%, not more than about 1.5%, not more than about 2%, not more than about 3% or not more than about 4%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of FYN comparable to that of a reference kinase inhibitor. In some embodiments, the irreversible BTK inhibitor has a percent inhibition of FYN that is not more than that observed for a reference kinase inhibitor. In some embodiments, the irreversible BTK inhibitor has a percent inhibition of FYN that is about 15-25%. In some embodiments, the irreversible BTK inhibitor has a percent inhibition of FYN that is about 15-20%. In some embodiments, the irreversible BTK inhibitor has a percent inhibition of FYN that is about 17-20%. In some embodiments, the irreversible BTK inhibitor has a percent inhibition of FYN that is not more than about 15%, not more than about 16%, not more than about 17%, not more than about 18%, not more than about 19%, not more than about 20%, not more than about 21%, not more than about 22% or not more than about 23%. In some embodiments, the reference kinase inhibitor is Compound 2. In some embodiments, the percent inhibition of the reference kinase inhibitor is that shown for Compound 2 in Example 2.

In some embodiments, the irreversible BTK inhibitor has a percent inhibition of BRAF comparable to that of a reference kinase inhibitor. In some embodiments, the irreversible BTK inhibitor has a percent inhibition of BRAF that is not more than that observed for a reference kinase inhibitor. In some embodiments, the irreversible BTK inhibitor has a percent inhibition of BRAF that is about 0-10%. In some embodiments, the irreversible BTK inhibitor has a percent inhibition of BRAF that is about 0.1-5%. In some embodiments, the irreversible BTK inhibitor has a percent inhibition of BRAF that is about 0.2-3%. In some embodiments, the irreversible BTK inhibitor has a percent inhibition of BRAF that is not more than about 0.1%, not more than about 0.2%, not more than about 0.3%, not more than about 0.4%, not more than about 0.5%, not more than about 0.6%, not more than about 0.7%, not more than about 0.8%, not more than about 0.9%, not more than about 1%, not more than about 2%, not more than about 3%, not more than about 4% or not more than about 5%. In some embodiments, the reference kinase inhibitor is Compound 2. In some embodiments, the percent inhibition of the reference kinase inhibitor is that shown for Compound 2 in Example 2.

Compound 1 is an Irreversible BTK Inhibitor

As described above, Bruton's tyrosine kinase (Btk) is a non-receptor tyrosine kinase with restricted cellular expression largely limited to B-lymphocytes, monocytes, and mast cells or basophils. Btk is a critical component of the B-cell receptor (BCR) signaling network and is crucial for B-cell development. Investigation has revealed that some B-cell malignancies, including CLL/SLL, depend on BCR signaling, suggesting that interruption of such signaling could be a promising therapeutic opportunity. Recently, clinical antitumor responses in various B-cell non-Hodgkin's lymphoma (NHL) and CLL/SLL have been reported with agents that inhibit spleen tyrosine kinase (Syk) and Btk, both components of the BCR signaling pathway.

Compound 1 is active in a variety of assays and therapeutic models demonstrating covalent, irreversible inhibition of BTK (in enzymatic and cellular assays). Compound 1 inhibits Btk activity by binding with high affinity to the adenosine triphosphate (ATP) binding site of Btk and forming a targeted covalent bond with the Btk protein, providing rapid, complete, and prolonged inhibition of Btk activity, both in vitro and in vivo.

Phosphorylation of the auto-phosphorylation site on Btk (Tyr223) and the Btk responsive site (Tyr1217) on PLCγ2 in Ramos cells, a human Burkitt lymphoma cell line, was inhibited by Compound 1 with an effective concentration required for 50% inhibition ($EC_{50}$) of 1 nM to 10 nM. Compound 1 demonstrates a high degree of selectivity in cellular assay systems against related kinases.

In single dose studies in healthy subjects, Compound 1 evidenced adequate safety, predictable pharmacokinetics (PK), and, at doses greater than 0.5 mg/kg, 80% to 100% occupancy of the Btk receptor target in normal human peripheral blood B-cells. A phase I dose escalation study of a single agent of Compound 1 is currently being conducted in different hematologic malignancies, including CLL/SLL.

Anti-CD20 Antibodies

CD20, the first B-cell specific antigen defined by the monoclonal antibody tositumomab, plays a critical role in B-cell development. Human CD20 is a 297 amino acid (30- to 35-kDa) phosphoprotein with four transmembrane domains encoded by the gene MS4A1 located on chromosome 11q12.2. CD20 plays a critical role in B-cell development and is a biomarker for immunotherapies targeting B-cell derived diseases. CD20 is an integral membrane protein expressed by B lymphocytes in early stages of differentiation and by most B cell lymphomas, but not by differentiated plasma cells. CD20 remains on the membrane of B cells without dissociation or internalization upon antibody binding. CD20 functions though binding to the Src family of tyrosine kinases, such as Lyn, Fyn and Lck, and believed to be involved as a result in the phosphorylation cascade of intracellular proteins. Anti-CD20 antibodies are broadly classified into type I and type II antibodies. Both types of anti-CD 20 antibodies exhibit equal ability in activating Fc-FcγR interactions such as antibody-dependent cellular cytotoxicity (ADCC) and phagocytosis. Type I anti-CD20 antibodies redistribute CD20 into membrane lipid rafts and potently activate complement-dependent cytotoxicity (CDC). Type II anti-CD20 antibodies weakly activate CDC but more potently induce direct programmed cell death.

In some embodiments, the present invention encompasses the recognition that the combination of a BTK inhibitor, i.e. Compound 1, in combination with an anti-CD20 antibody is useful in treating BTK-mediated diseases or disorders. Accordingly, in some embodiments, the present invention comprises a method of treating a BTK-mediated disease or disorder, the method comprising administering to a patient in need thereof Compound 1 in combination with an anti- CD20 antibody. A person of ordinary skill in the art can readily identify and select additional anti-CD20 antibodies that are useful in the present invention. For example, in some embodiments, such antibodies are described, for example, in U.S. Pat. Nos. 8,153,125, 8,147,832, 8,101,179, 8,084,582, 8,057,793 and 7,879,984, and U.S. Patent Publication Nos. 2011/0129412, 2012/0183545, 2012/0134990 and 2012/0034185.

In some embodiments, an anti-CD20 antibody for use in the present invention is a type I antibody. In some embodiments, an anti-CD20 for use in the present invention is a type II antibody.

In some embodiments, an anti-CD20 antibody is an antibody that binds to a CD20 epitope selected from $^{170}$ANPS$^{173}$ and $^{182}$YCYSI$^{185}$.

In some embodiments, an anti-CD20 antibody has a binding affinity ($K_d$) for an epitope of CD20 of less than 12 nM, less than 11 nM, less than 10 nM, less than 9 nM, less than 8 nM, less than 7 nM, less than 6 nM, less than 5 nM, less than 4 nM, less than 3 nM, less than 2 nM or less than 1 nM.

Rituximab is but one example of an anti-CD20 antibody. In some embodiments, an anti-CD20 antibody for use in the present invention includes, for example, rituximab (Rituxan® or MabThera®), Gazyva® (i.e., obinutuzumab) and Arzerra® (ofatumumab). For ease of reference, provided methods and regimens detailed herein refer to an exemplary anti-CD20 antibody (i.e., rituximab); however, such reference is not intended to limit the present invention to a single anti-CD20 antibody. Indeed, all references to rituximab, or a biosimilar thereof, are to be read by a person skilled in the art to encompass the class of anti-CD20 antibodies. For example, it will be appreciated that the anti-CD20 antibodies ofatumumab (Arzerra®) or obinutuzumab (Gazyva®) can instead be administered in each instance where reference is made to rituximab. Thus, in some embodiments, provided methods comprise administering Compound 1 and ofatumumab. In some such embodiments, ofatumumab is administered in 12 doses according to the following schedule: 300 mg initial dose, followed 1 week later by 2000 mg dose weekly for 7 doses, followed 4 weeks later by 2000 mg every 4 weeks for 4 doses. In some embodiments, provided methods comprise administering Compound 1 and obinutuzumab. In some such embodiments, obinutuzumab is administered for six 28-day cycles as follows: 100 mg on day 1, cycle 1; 900 mg on day 2 cycle 1; 1000 mg on days 8 and 15 of cycle 1; and 1000 mg on day 1 of cycles 2-6. Accordingly, in some embodiments, the term "rituximab" encompasses all corresponding anti-CD20 antibodies that fulfill the requirements necessary for obtaining a marketing authorization as an identical or biosimilar product in a country or territory selected from the group of countries consisting of the USA, Europe and Japan.

In some embodiments, an anti-CD20 antibody has the same or similar activity as rituximab, or a biosimilar thereof. In some embodiments, an anti-CD20 antibody binds to the same or similar region or epitope as rituximab or a fragment thereof. In some embodiments, an anti-CD20 antibody competes with the binding of rituximab or a fragment thereof to CD20. In some embodiments, an anti-CD20 antibody is bioequivalent to rituximab or a fragment thereof. In some embodiments, an anti-CD20 antibody is a biosimilar of rituximab or a fragment thereof. In some embodiments, an anti-CD20 antibody is a variant or derivative of rituximab, including functional fragments, derivatives, or antibody conjugates.

Rituximab

Rituximab (Rituxan® or MabThera®) is a genetically engineered cytolytic, chimeric murine/human monoclonal IgG$_1$ kappa antibody directed against the CD20 cell-surface molecule present in normal B lymphocytes and B-cell CLL and in most forms of non-Hodgkin's B-cell lymphomas. Rituximab has a binding affinity for the CD20 antigen of approximately 8.0 nM. Rituximab can induce complement-dependent cellular cytotoxicity (CDC) and anti-body-dependent cellular cytotoxicity (ADCC), leading to its clinical activity against lymphoma cells. Rituximab can also lead to apoptosis of B cells upon binding to CD20, thereby leading to direct inhibition of cellular growth.

Rituximab is produced by mammalian cell (Chinese Hamster Ovary) suspension culture in a nutrient medium containing the antibiotic gentamicin. Gentamicin is not detectable in the final product. Rituximab is a sterile, clear, colorless, preservative-free liquid concentrate for intravenous administration. Rituximab is supplied at a concentration of 10 mg/mL in either 100 mg/10 mL or 500 mg/50 mL single-use vials. Rituximab is formulated in polysorbate 80 (0.7 mg/mL), sodium citrate dihydrate (7.35 mg/mL), sodium chloride (9 mg/mL) and water for injection. The pH of Rituxan® (or MabThera®) is 6.5

Rituximab has been investigated in clinical studies and approved for treatment of patients with CLL in combination with fludarabine and cyclophosphamide, as well as patients with rheumatoid arthritis in combination with methotrexate. Rituximab is also approved for treatment of non-Hodgkin's lymphoma, Wegener's Granulomatosis and Microscopic Polyangiitis.

In some embodiments, provided methods comprise administering to a patient in need thereof a combination of Compound 1 and rituximab, wherein the patient is further treated with fludarabine and cyclophosphamide in accordance with the approved indications.

I. General Dosing Protocol

As described herein, provided methods comprise administering Compound 1 and an anti-CD20 antibody (e.g., rituximab, ofatumumab, obinutuzumab, etc.) to a patient in need thereof. Such methods optionally further comprise administering either (i) fludarabine and cyclophosphamide or (ii) bendamustine. It will be appreciated that each of the therapeutic agents (i.e., Compound 1, anti-CD20 antibody, fludarabine, cyclophosphamide and bendamustine) can be administered simultaneously or sequentially (e.g., Compound 1 can be administered before, during or after an anti-CD20 antibody and/or either (i) fludarabine and cyclophosphamide or (ii) bendamustine and vice versa) as part of a dosing regimen. For example, Compound 1 may be administered one or more hours, days or weeks before administration of an anti-CD20 antibody. In some embodiments, Compound 1 and an anti-CD20 antibody may be administered one or more hours, days or weeks before administration of either (i) fludarabine and cyclophosphamide or (ii) bendamustine.

In some embodiments, the present invention provides methods for treating, stabilizing or lessening the severity or progression of one or more diseases or conditions associated with BTK. In some embodiments, the present invention provides methods for preventing the progression of a disease or disorder associated with BTK. In some embodiments, the disease or disorder associated with BTK is selected from chronic lymphocytic leukemia (CLL) and small lymphocytic lymphoma (SLL).

In some embodiments, the disease or disorder associated with BTK is refractory CLL. In some embodiments, the disease or disorder associated with BTK is relapsed CLL. In some embodiments, the disease or disorder associated with BTK is refractory SLL. In some embodiments, the disease or disorder associated with BTK is relapsed SLL.

In some embodiments, provided methods comprise administering to a patient in need thereof Compound 1 in combination with rituximab. In some such embodiments, each of Compound 1 and rituximab is administered as a composition further comprising one or more pharmaceutically acceptable excipients. In some embodiments, provided methods comprise administering each of Compound 1, rituximab, fludarabine and cyclophosphamide. In some such embodiments, each of Compound 1, rituximab, fludarabine and cyclophosphamide is administered as a composition further comprising one or more pharmaceutically acceptable excipients. In some embodiments, provided methods comprise administering each of Compound 1, rituximab and bendamustine. In some such embodiments, each of Compound 1, rituximab and bendamustine is administered as a composition further comprising one or more pharmaceutically acceptable excipients.

In some embodiments, provided methods comprise administering to a patient in need thereof a therapeutically effective amount of Compound 1 in combination with a therapeutically effective amount of rituximab. Accordingly, in some embodiments, the present invention provides a method of treating, stabilizing or lessening the severity or progression of one or more diseases associated with BTK, the method comprising administering to a patient in need thereof a therapeutically effective amount of Compound 1 in combination with a therapeutically effective amount of rituximab. In some embodiments, provided methods comprise administering to a patient in need thereof therapeutically effective amounts of each of Compound 1, rituximab, fludarabine and cyclophosphamide. In some embodiments, provided methods comprise administering to a patient in need thereof therapeutically effective amounts of each of Compound 1, rituximab and bendamustine.

In some embodiments, provided methods comprise administering Compound 1 in combination with rituximab, wherein Compound 1 is administered once daily ("QD"). In some embodiments, provided methods comprise administering Compound 1 in combination with rituximab, wherein Compound 1 is administered twice daily ("BID"). For purposes of clarity, administration of a 375 mg dose of Compound 1 "BID" means that the patient is administered two separate doses of 375 mg in one day. In some embodiments, provided methods comprise administering each of Compound 1, rituximab, fludarabine and cyclophosphamide, wherein Compound 1 is administered twice daily ("BID"). In some embodiments, provided methods comprise administering each of Compound 1, rituximab and bendamustine, wherein Compound 1 is administered twice daily ("BID").

In some embodiments, provided methods comprise administering Compound 1 in combination with rituximab, wherein rituximab is administered once during a 28-day cycle. In some embodiments, provided methods comprise administering Compound 1 in combination with rituximab, wherein rituximab is administered on cycle 1 day 1 or day 2. In some embodiments, provided methods comprise administering Compound 1 in combination with rituximab, wherein rituximab is administered on day 1 of a 28-day cycle. In some such embodiments, rituximab is administered on day 1 of cycles 2-6. In some embodiments, rituximab is administered on day 1 of cycles 2-5. In some embodiments, rituximab is administered on day 1 of cycles 2-4. In some embodiments, rituximab is administered on day 1 of cycles 2-3. In some embodiments, provided methods comprise administering each of Compound 1, rituximab, fludarabine and cyclophosphamide, wherein rituximab is administered once during a 28-day cycle. In some such embodiments, rituximab is administered on day 1 or day 2 of a 28-day cycle.

In some embodiments, provided methods comprise administering each of Compound 1, rituximab and bendamustine, wherein rituximab is administered once during a 28-day cycle. In some such embodiments, rituximab is administered on day 1 or day 2 of a 28-day cycle.

In some embodiments, provided methods comprise administering Compound 1 in combination with rituximab, wherein Compound 1 is administered twice daily and rituximab is administered once during a 28-day cycle. In some embodiments, provided methods comprise administering Compound 1 in combination with rituximab, wherein Compound 1 is administered twice daily and rituximab is administered on cycle 1 day 1 or day 2. In some embodiments, provided methods comprise administering Compound 1 in combination with rituximab, wherein Compound 1 is administered twice daily and rituximab is administered on day 1 of a 28-day cycle. In some such embodiments, rituximab is administered on day 1 of cycles 2-6. In some embodiments, provided methods comprise administering each of Compound 1, rituximab, fludarabine and cyclophosphamide, wherein Compound 1 is administered twice daily and rituximab is administered once during a 28-day cycle. In some such embodiments, rituximab is administered on day 1 or day 2 of a 28-day cycle.

In some embodiments, provided methods comprise administering each of Compound 1, rituximab and bendamustine, wherein Compound 1 is administered twice daily and rituximab is administered once during a 28-day cycle. In some such embodiments, rituximab is administered on day 1 or day 2 of a 28-day cycle.

In some embodiments, each of Compound 1 and rituximab is administered as pharmaceutically acceptable compositions. In some embodiments, a pharmaceutically acceptable composition comprising Compound 1 is formulated as an oral dosage form. In some embodiments, such oral dosage forms are capsules. In some embodiments, the pharmaceutically acceptable composition comprising rituximab is formulated as an intravenous composition. In some embodiments, fludarabine, cyclophosphamide and bendamustine are formulated as intravenous compositions.

In some embodiments, a pharmaceutically acceptable composition comprising Compound 1 comprises from about 5% to about 60% of Compound 1, or a pharmaceutically acceptable salt thereof, based upon total weight of the composition. In some embodiments, a pharmaceutically acceptable composition comprising Compound 1 comprises from about 5% to about 15% or about 7% to about 15% or about 7% to about 10% or about 9% to about 12% of Compound 1, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of Compound 1, based upon total weight of the formulation. In certain embodiments, provided regimens comprise administering to a patient in need thereof a pharmaceutically acceptable composition comprising from about 6%, about 7%, about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of Compound 1, based upon total weight of given composition or formulation.

Rituximab is commercially available as a 10 mg/mL solution comprising sodium citrate, polysorbate 80, sodium chloride, sodium hydroxide, hydrochloric acid and water. Commercially available vials comprise either 100 mg/10 mL or 500 mg/50 mL.

In some embodiments, a pharmaceutically acceptable composition comprises from about 1 mg/mL to about 4 mg/mL rituximab. In some embodiments, a pharmaceutically acceptable composition comprises from about 1 mg/mL, about 2 mg/mL, about 3 mg/mL or about 4 mg/mL rituximab. In some embodiments, a pharmaceutically acceptable composition comprises 10 mg/mL.

Fludarabine (Fludara®) is commercially available as a vial of sterile lyophilized solid cake containing 50 mg of fludarabine phosphate, 50 mg of mannitol and sodium hydroxide to adjust pH to 7.7. The pH range for the final solution is 7.2-8.2. The solid cake is reconstituted with 2 mL of Sterile Water for Injection USP, which results in a solution containing 25 mg/mL of fludarabine phosphate intended for intravenous administration.

Cyclophosphamide (Cytoxan®) is commercially available as a sterile powder which may be prepared for parenteral use by infusion by reconstituting, for example, in 0.9% sterile sodium chloride (5 mL per 100 mg anhydrous powder). Alternative solutions for reconstitution may be found, for example, in the package insert.

Bendamustine (Treanda®) is commercially available as a single-use vial containing 100 mg of bendamustine hydrochloride as a lyophilized powder. The powder is reconstituted with 20 mL of Sterile Water for Injection USP to a final concentration of 5 mg/mL. Immediatly prior to infusion, the 5 mg/mL reconstituted solution is transferred to a 500 mL infusion bag containing 0.9% Sodium Chloride Injection USP. Alternatively, the 5 mg/mL reconstituted solution may be transferred to a 500 mL infusion bag containing 2.5% Dextrose/0.45% Sodium Chloride Injection USP. The final concentration of bendamustine hydrochloride in the infusion bag should be about 0.2-0.6 mg/mL.

In some embodiments, provided methods comprise administering Compound 1 in combination with rituximab daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, a treatment regimen comprises at least one 28-day cycle. As used herein, the term "28-day cycle" means that provided treatment regimens are administered to a patient in need thereof for 28 consecutive days. In some embodiments, the combination of Compound 1 and rituximab is administered for at least two, at least three, at least four, at least five or at least six 28-day cycles. In some embodiments, the combination of Compound 1 and rituximab is administered for at least seven, at least eight, at least nine, at least ten, at least eleven or at least twelve 28-day cycles. In some embodiments, the combination of Compound 1 and rituximab is administered for at least thirteen, at least fourteen, at least fifteen, at least sixteen, at least seventeen, at least eighteen, at least nineteen or at least twenty 28-day cycles. In some embodiments, the combination of Compound 1 and rituximab is administered to a patient for the duration of the patient's life.

In some embodiments, provided methods comprise administering to a patient in need thereof each of Compound 1, rituximab, fludarabine and cyclophosphamide, wherein each of rituximab, fludarabine and cyclophosphamide is administered for at least one, two, at least three, at least four, at least five or at least six 28-day cycles.

In some embodiments, the combination of Compound 1 and rituximab is administered for at least six 28-day cycles, and Compound 1 is administered for at least one additional 28-day cycle. In some embodiments, the combination of Compound 1 and rituximab is administered for at least six 28-day cycles, and Compound 1 is administered for an additional two, three, four, five, six, seven, eight, nine, ten, eleven, twelve, thirteen or fourteen 28-day cycles. In some embodiments, the combination of Compound 1 and rituximab is administered for at least six 28-day cycles, and Compound 1 is administered for the duration of the patient's life. In some embodiments, Compound 1 is administered on days 1 through 28 (for example, one dose each day or two doses each day) of one or more 28-day cycles and rituximab is administered on day 1 of a 28-day cycle. In some embodiments, Compound 1 is administered on days 1 through 28 of one or more 28-day cycles and rituximab is administered on day 1 or day 2 of a 28-day cycle.

In some embodiments, two adjacent 28-day cycles may be separated by a rest period. Such a rest period may be one, two, three, four, five, six, seven or more days during which the patient is not administered either or both Compound 1 and rituximab. In a preferred embodiment, two adjacent 28-day cycles are continuous.

In some embodiments, provided methods comprise administering to a patient in need thereof Compound 1 in combination with rituximab, wherein the patient has failed at least one prior therapy. In some embodiments, provided methods comprise administering to a patient in need thereof Compound 1, rituximab, fludarabine and cyclophosphamide, wherein the patient has failed at least one prior therapy. In some embodiments, provided methods comprise administering to a patient in need thereof Compound 1, rituximab and benmustine, wherein the patient has failed at least one prior therapy.

Unit Dosage Forms

Pharmaceutical compositions for use in the present invention may be prepared as a unit dosage form. A person of ordinary skill will appreciate that the unit dosage forms described herein refer to an amount of a component in its free base form. A person skilled in the art will further appreciate that, when a pharmaceutical composition comprises a salt form of one component, for example, a besylate salt form of Compound 1, the amount of the salt form present in the composition is an amount that is equivalent to a unit dose of the free base of the component (i.e., of Compound 1). For example, a pharmaceutical composition comprising a besylate salt of Compound 1 would contain 34.97 mg of the besylate salt form necessary to deliver an equivalent 25 mg unit dose of the free base of Compound 1.

In some embodiments, provided methods comprise administering to a patient in need thereof a therapeutically effective amount of Compound 1, wherein the therapeutically effective amount of Compound 1 is about 250 mg to about 1250 mg. In some embodiments, the therapeutically effective amount of Compound 1 is administered as one or more discreet doses. For example, in some embodiments, a therapeutically effective amount of Compound 1 is 250 mg, wherein the therapeutically effective amount is administered as 125 mg twice daily (BID). In some embodiments, a therapeutically effective amount of Compound 1 is 500 mg, wherein the therapeutically effective amount is administered as 250 mg twice daily (BID). In some embodiments, a therapeutically effective amount of Compound 1 is 750 mg, wherein the therapeutically effective amount is administered as 375 mg twice daily (BID). In some embodiments, a therapeutically effective amount of Compound 1 is 1000 mg, wherein the therapeutically effective amount is administered as 500 mg twice daily (BID).

In some embodiments, provided methods comprise administering to a patient in need thereof a therapeutically effective amount of Compound 1, wherein the therapeutically effective amount of Compound 1 is about 125 mg to about 1250 mg, or about 125 mg to about 1125 mg, or about 125 mg to about 1000 mg, or about 125 mg to about 875 mg, or about 125 mg to about 750 mg, or about 125 mg to about 625 mg, or about 125 mg to about 500 mg, or about 125 mg to about 375 mg, or about 125 mg to about 250 mg, or about 250 mg to about 1250 mg, or about 250 mg to about 1125 mg, or about 250 mg to about 1000 mg, or about 250 mg to about 875 mg, or about 250 mg to about 750 mg, or about 250 mg to about 625 mg, or about 250 mg to about 500 mg, or about 250 mg to about 375 mg, or about 375 mg to about 1250 mg, or about 375 mg to about 1125 mg, or about 375 mg to about 1000 mg, or about 375 mg to about 875 mg, or about 375 mg to about 750 mg, or about 375 mg to about 625 mg, or about 375 mg to about 500 mg, or about 500 mg to about 1250 mg, or about 500 mg to about 1125 mg, or about 500 mg to about 1000 mg, or about 500 mg to about 750 mg, or about 500 mg to about 625 mg, or about 625 mg to about 1250 mg, or about 625 mg to about 1125 mg, or about 625 mg to about 1000 mg, or about 625 mg to about 875 mg, or about 625 mg to about 750 mg, or about 750 mg to about 1250 mg, or about 750 mg to about 1125 mg, or about 750 mg to about 1000 mg, or about 875 mg to about 1250 mg, or about 875 mg to about 1125 mg, or about 875 mg to about 1000 mg.

In some embodiments, provided methods comprise administering to a patient in need thereof a therapeutically effective amount of Compound 1, wherein the therapeutically effective amount of Compound 1 is about 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1000 mg, 1005 mg, 1010 mg, 1015 mg, 1020 mg, 1025 mg, 1030 mg, 1035 mg, 1040 mg, 1045 mg, 1050 mg, 1055 mg, 1060 mg, 1065 mg, 1070 mg, 1075 mg, 1080 mg, 1085 mg, 1090 mg, 1095 mg, 1100 mg, 1105 mg, 1110 mg, 1115 mg, 1120 mg, 1125 mg, 1130 mg, 1135 mg, 1140 mg, 1145 mg, 1150 mg, 1155 mg, 1160 mg, 1165 mg, 1170 mg, 1175 mg, 1180 mg, 1185 mg, 1190 mg, 1195 mg, 1200 mg, 1205 mg, 1210 mg, 1215 mg, 1220 mg, 1225 mg, 1230 mg, 1235 mg, 1240 mg, 1245 mg or 1250 mg.

In some embodiments, provided methods comprise administering to a patient in need thereof a pharmaceutical composition comprising a unit dose of Compound 1 in combination with rituximab. In some such embodiments, the unit dose of Compound 1 is about 25 mg, about 50 mg, about 75 mg, about 100 mg, about 125 mg, about 150 mg, about 175 mg, about 200 mg, about 225 mg or about 250 mg.

In some embodiments, provided methods comprise administering to a patient in need thereof a pharmaceutical composition comprising rituximab, wherein rituximab is administered as an infusion at a rate of 50 mg/hr. In some embodiments, the infusion rate of rituximab is increased by 50 mg/hr every 30 minutes, to a maximum of 400 mg/hr. In some embodiments, the infusion rate of rituximab is increased by 100 mg/hr every 30 minutes, to a maximum of 400 mg/hr. Accordingly, in some embodiments, the infusion rate of rituximab is 100 mg/hr. In some embodiments, the infusion rate of rituximab is 150 mg/hr. In some embodiments, the infusion rate of rituximab is 200 mg/hr. In some embodiments, the infusion rate of rituximab is 250 mg/hr. In some embodiments, the infusion rate of rituximab is 300 mg/hr. In some embodiments, the infusion rate of rituximab is 350 mg/hr. In some embodiments, the infusion rate of rituximab is 400 mg/hr.

II. Use of Compounds and Pharmaceutically Acceptable Compositions

Compound 1 and compositions described herein are generally useful for the inhibition of protein kinase activity of one or more enzymes. Examples of kinases that are inhibited by Compound 1 and compositions described herein and against which the methods described herein are useful include BTK and other TEC-kinases, including ITK, TEC, BMX and RLK, or a mutant thereof.

Bruton's tyrosine kinase ("BTK"), a member of TEC-kinases, is a key signaling enzyme expressed in B-lymphocytes, monocytes, and mast cells or basophils. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr. Op. Imm., 2000, 276-281; Schaeffer and Schwartzberg, Curr. Op. Imm. 2000, 282-288). In addition, BTK plays a role in a number of other hematopoietic cell signaling pathways, e.g., Toll like receptor (TLR) and cytokine receptor-mediated TNF-α production in macrophages, IgE receptor (Fc_epsilon_RI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek et al. (1998), Current Biology 8(20): 1137-1140.

Patients with inherited inactivating mutations in BTK have a profound block in B-cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B-cells and greatly decreased serum levels of IgM and IgG3. BTK deletion in mice has a profound effect on B-cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc_epsilon_RI). BTK deficient murine mast cells have reduced degranulation and decreased production of proinflammatory cytokines following Fc_epsilon_RI cross-linking (Kawakami et al. Journal of Leukocyte Biology 65: 286-290).

Compound 1 is an inhibitor of BTK and therefore useful for treating one or more disorders associated with activity of BTK. Thus, in some embodiments, the present invention provides a method of treating, stabilizing or lessening the severity or progression of a BTK-mediated disorder comprising the step of administering to a patient in need thereof Compound 1 in combination with rituximab.

Chronic Lymphocytic Leukemia and Small Lymphocytic Lymphoma

The B-cell disorders chronic lymphocytic leukemia (CLL) and small lymphocytic lymphoma (SLL) represent two ends of a spectrum of the same disease process differing in the degree of blood/marrow involvement (CLL) versus lymph node involvement (SLL). CLL is a lymphoproliferative malignancy characterized by progressive accumulation of morphologically mature but functionally incompetent lymphocytes in the blood, bone marrow, and lymphoid tissues. It affects mainly elderly individuals with the median age at presentation of 65 to 70 years. The clinical course of CLL ranges from indolent disease with long-term survival over 12 years to aggressive disease with median survival of 2 years.

Chronic lymphocytic leukemia is the most common leukemia in the U.S. and is typically characterized immunophenotypically as CD5+, CD23+, CD10−, CD19+, CD20 dim, sIg dim, and cyclin D1− (the latter point a distinguishing feature from mantle cell lymphoma). Chronic lymphocytic leukemia must also be distinguished from monoclonal B lymphocytosis (absolute monoclonal B-cell count <5000/µL, and absence of adenopathy or other clinical features of lymphoproliferative disorder). The understanding of CLL/SLL biology and prognostic factors, and advances in formulating a risk-stratified approach to treatment of CLL/SLL have been recently reviewed by Lanasa, Furman, and the National Comprehensive Cancer Network NHL panel.

The cellular expression of Btk is restricted and largely limited to B-lymphocytes, monocytes, and mast cells or basophils. Investigation has revealed that some B-cell lymphomas and CLL/SLL depend on BCR signaling, suggesting that interruption of such signaling could be a promising therapeutic opportunity Recently it has been reported that half of all CLL retain BCR signaling in vitro and that immunoglobulin heavy gene somatic mutation (IgVH) is an important determinant of BCR responsiveness. Indeed, the mutational status of the BCR in CLL is one of the strongest predictors of disease progression, as aggressive disease typically displays BCR encoded by unmutated immunoglobulin variable heavy chains.

Two groups have reported that mutated and unmutated CLL cells respond differentially to IgM ligation of the BCR, with unmutated, but not mutated, CLL cells responding to BCR stimulation with increased global tyrosine phosphorylation and by up-regulating several genes associated with cell cycle regulation and allowing cell growth and expansion. These data highlight the differential role that BCR signaling plays in CLL physiology depending on IgVH mutational status and may suggest a possible differential responsiveness of CLL to inhibitors of BCR signaling. Other in vitro studies have reported that specific Btk inhibition with the investigational agent PCI-32765 produced substantially more apoptosis and cytotoxicity in CLL cells relative to normal B-cells; as well as inducing apoptosis in the face of anti-apoptotic micro-environmental signals, reduction of secretion of chemokines CCL3 and CCL4, and reduction of chemotaxis towards the chemokines CXCL12 and CXCL13. Detailed studies of the pathophysiologic role of Btk in the origin and/or maintenance of Waldenstrom's macroglobulinemia (WM) have not yet been reported. However, a recent report investigating transgenic mouse models demonstrated that constitutively active Btk expression resulted in selective expansion or survival of B-1 cells that were driven into germinal center independent plasma cell differentiation, as evidenced by increased numbers of IgM+ plasma cells in spleen and bone marrow and significantly elevated serum IgM. Anti-nucleosome autoantibodies and glomerular IgM deposition were also observed. However, one study of sequence analysis in 19 WM patients with hypogammaglobulinemia G and/or A failed to find any novel variants in the promoter, flanking introns, or exons of Btk.

Allogeneic stem cell transplant is the only potentially curative treatment for CLL, but 70% of affected patients are ≥65 years of age at the time of diagnosis, have co-morbid conditions limiting eligibility for such therapy, and may exhibit a prolonged natural history with or without specific treatment. The actual prognosis of CLL is variable and dependent principally on clinical stage and certain genetic and molecular features. Both the Rai and Binet clinical staging systems are able to distinguish patient prognostic groups with median OSs ranging from 19 months in the most advanced stage (thrombocytopenia) to >150 months in the earliest stage (blood and marrow lymphocytosis without adenopathy, organomegaly, or defined anemia/thrombocytopenia). Classification by the presence or absence of IgVH and by interphase fluorescent in situ hybridization (iFISH) analysis for probed-for acquired chromosomal abnormalities adds additional prognostic discrimination to clinical staging, with unmutated IgVH and del(11q) and del(17p) cytogenetics predicting poorer outcome.

The CLL treatment algorithm is complex and requires first the decision to treat (e.g., presence of symptoms such as fatigue or night sweats; bulky adenopathy/organomegaly; progressive anemia/thrombocytopenia); and second, choice of the treatment regimen, usually involving one or more: purine nucleosides (fludarabine), alkylating agents (cyclophosphamide, chlorambucil, bendamustine), corticosteroids, anti-CD20 monoclonal antibodies (rituximab/ofatumumab), or anti-CD52 monoclonal antibodies (alemtuzumab). The choice of specific therapies depends on the patient's age, disease pattern (eg, primarily nodal versus non-nodal), anticipated drug tolerance and contraindications, and presence or absence of adverse prognostic features such as del(11q) or del(17p). Despite numerous therapies, treatment options are eventually limited by drug toxicities and resistance, and patients who do not succumb to other maladies endure progressive complications relating to cytopenias, the effects of lymphadenopathy and organomegaly, systemic symptoms, and infectious complications. Given the often elderly character of the patient population, an orally available, well tolerated treatment that exploits a novel weakness of CLL would be welcome.

Rationale for Targeting Btk and Combinations with Rituximab in CLL and SLL

Strategies specifically targeting B-cells, for example the B-cell depleting anti-CD20 monoclonal antibodies rituximab and ofatumumab, have demonstrated clinical efficacy in B-cell lymphoma and CLL. Spleen tyrosine kinase (Syk) is a kinase in the BCR signaling pathway proximal to Btk. Inhibition of Syk with the orally available Syk inhibitor fostamatinib disodium produced clinical responses in DLBCL, CLL, and mantle cell lymphoma. Most tellingly, clinical proof of concept for Btk inhibition has been demonstrated by clinical investigations of the orally available Btk inhibitor PCI-32765, which have reported objective anti-tumor responses in patients with DLBCL; mantle cell, marginal zone/mucosa-associated lymphoid tissue (MALT), and follicular lymphoma (FL), WM, and CLL/SLL, with good tolerability.

Thus, based on the critical importance of BCR signaling mediated through Btk for the survival and proliferation of various malignant B-cells; Btk's limited cellular expression in B-cells, macrophages, and monocytes; and demonstrated pre-clinical and early clinical proofs of concept that Btk inhibition produces salutary anti-lymphoma, CLL, and WM effects with acceptable clinical tolerability, targeting Btk with a selective Btk inhibitor is a promising and appropriate therapeutic strategy to investigate further in the clinic. Compound 1, as its besylate salt, has been shown in recent studies to be safe and effective against CLL as a single agent therapeutic. As of Sep. 11, 2012, 35 out of 43 patients with CLL and have experienced stable disease and continue to on treatment with N-(3-(5-fluoro-2-(4-(2-methoxyethoxy)phenylamino)pyrimidin-4-ylamino)phenyl)acrylamide besylate monotherapy. 15 of 23 patients have experienced reductions in lymph node size, and 28 of 33 patients have experienced early increases in absolute lymphocyte counts (ALC). See U.S. patent application Ser. No. 13/661,678 and International Patent Application No. PCT/US2012/062133, both filed on Oct. 26, 2012, each of which is hereby incorporated by reference in its entirety. Such data strongly support the use of a BTK inhibitor, and Compound 1 in particular, for treating CLL. Compound 1 is generally well tolerated as a single agent at up to 750 mg PO QD and the maximum tolerated dose (MTD) has not yet been reached. Studies are ongoing and additional dose levels currently being investigated include: 1000 mg QD, 1250 mg QD, 375 mg BID and 500 mg BID.

Rituximab has also been shown to exhibit good activity against relapsed/refractory CLL patients. In one study, rituximab, in combination with fludarabine/cyclophosphamide, was evaluated in 408 patients with CLL and showed an 86% response rate, as compared to the 73% response rate observed for fludarabine/cyclophosphamide alone. The median progression-free survival was 39.8 months, as compared to 31.5 months observed for fludarabine/cyclophosphamide alone. Accordingly, in some embodiments, the present invention encompasses the recognition that a BTK inhibitor such as Compound 1 in combination with rituximab is useful in the treatment of CLL and SLL. Compound 1 either as a single agent or in combination, may be found to be efficacious in CLL patients, including but not limited to those who had expressed one or more of the following prognostic/genetic markers and cytogenetic risk factors: deletions of chromosome 11q, 17p or 13q, or Trisomy 12 and 14q, zeta-chain-associated protein kinase 70 (ZAP 70) or immunoglobulin heavy chain variable region (IgVH) un-mutated.

In some embodiments, the present invention provides methods of treating, stabilizing or lessening the severity or progression of one or more diseases and conditions associated with BTK comprising administering to a patient in need thereof Compound 1 in combination with rituximab.

III. Methods of Treating Diseases Disorders Associated with BTK

In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof Compound 1 in combination with rituximab. In some embodiments, provided methods comprise administering to a patient in need thereof each of Compound 1, rituximab, fludarabine and cyclophosphamide. In some embodiments, provided methods comprise administering to a patient in need thereof each of Compound 1, rituximab and bendamustine.

In some embodiments, provided methods comprise administering to a patient in need thereof a composition comprising Compound 1 in combination with a composition comprising rituximab. In some embodiments, the composition comprising Compound 1 further comprises one or more pharmaceutically acceptable excipients. In some such embodiments, the composition comprising Compound 1 is formulated as an oral dosage form. In some embodiments, the oral dosage form is a capsule. In some embodiments, provided methods comprise administering to a patient in need thereof compositions comprising each of Compound 1, rituximab, fludarabine and cyclophosphamide. In some embodiments, provided methods comprise administering to a patient in need thereof compositions comprising each of Compound 1, rituximab and bendamustine.

In some embodiments, the composition comprising rituximab further comprises one or more pharmaceutically acceptable excipients. In some such embodiments, the composition comprising rituximab is formulated as an intravenous dosage form.

In some embodiments, provided methods comprise administering to a patient in need thereof a unit dose of Compound 1 in combination with a unit dose of rituximab. In some embodiments, the unit dose of Compound 1 is about 25 mg, about 50 mg, about 75 mg, about 100 mg, about 125 mg, about 150 mg, about 175 mg, about 200 mg, about 225 mg or about 250 mg.

In some embodiments, provided methods comprise administering to a patient in need thereof a pharmaceutical composition comprising rituximab, wherein rituximab is administered as an infusion at a rate of 50 mg/hr. In some embodiments, the infusion rate of rituximab is increased by 50 mg/hr every 30 minutes, to a maximum of 400 mg/hr. In some embodiments, the infusion rate of rituximab is increased by 100 mg/hr every 30 minutes, to a maximum of 400 mg/hr. Accordingly, in some embodiments, the infusion rate of rituximab is 100 mg/hr. In some embodiments, the infusion rate of rituximab is 150 mg/hr. In some embodiments, the infusion rate of rituximab is 200 mg/hr. In some embodiments, the infusion rate of rituximab is 250 mg/hr. In some embodiments, the infusion rate of rituximab is 300 mg/hr. In some embodiments, the infusion rate of rituximab is 350 mg/hr. In some embodiments, the infusion rate of rituximab is 400 mg/hr.

In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof Compound 1 in combination with rituximab, wherein the patient has failed at least one prior therapy. In some embodiments, provided methods comprise administering to a patient in need thereof Compound 1, rituximab, fludarabine and bendamustine, wherein the patient has failed at least one prior therapy. In some embodiments, provided methods comprise administering to a patient in need thereof Compound 1, rituximab and bendamustine, wherein the patient has failed at least one prior therapy.

In some embodiments, provided methods comprise administering to a patient in need thereof about 500 mg to about 1250 mg Compound 1 in combination with about 375 mg/m$^2$ to about 500 mg/m$^2$ rituximab. In some embodiments, provided methods comprise administering to a patient in need thereof about 750 mg to about 1000 mg Compound 1 and about 375 mg/m$^2$ to about 500 mg/m$^2$ rituximab. In some embodiments, provided methods comprise administering to a patient in need thereof about 500 mg to about 1250 mg Compound 1, about 375 mg/m$^2$ to about 500 mg/m$^2$ rituximab, about 25 mg/m$^2$ fludarabine and about 250 mg/m$^2$ cyclophosphamide. In some embodiments, provided methods comprise administering to a patient in need thereof about 750 mg to about 1000 mg Compound 1, about 375 mg/m$^2$ to about 500 mg/m$^2$ rituximab and about 70 mg/m$^2$ bendamustine.

In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof about 375 mg BID to about 500 mg BID Compound 1 in combination with about 375 m g/m$^2$ to about 500 mg/m$^2$ rituximab. In some such embodiments, rituximab is administered once during a 28-day cycle. In some embodiments, provided methods comprise administering to a patient in need thereof about 250 mg to about 500 mg BID Compound 1, about 375 mg/m$^2$ to about 500 mg/m$^2$ rituximab, about 25 mg/m$^2$ fludarabine and about 250 mg/m$^2$ cyclophosphamide, wherein rituximab is administered on day 1 of a 28-day cycle. In some such embodiments, each of fludarabine and cyclophosphamide is administered on days 1-3 of a 28-day cycle. In some embodiments, provided methods comprise administering to a patient in need thereof about 750 mg to about 1000 mg Compound 1, about 375 mg/m$^2$ to about 500 mg/m$^2$ rituximab and about 70 mg/m$^2$ bendamustine, wherein rituximab is administered on day 1 of a 28-day cycle. In some such embodiments, bendamustine is administered on days 1 and 2 of a 28-day cycle.

In some embodiments, provided methods comprise administering to a patient in need thereof about 125 mg BID Compound 1 and about 375 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 125 mg BID Compound 1, about 375 mg/m$^2$ rituximab and about 70 mg/m$^2$ bendamustine.

In some embodiments, provided methods comprise administering to a patient in need thereof about 125 mg BID Compound 1 and about 500 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 125 mg BID Compound 1, about 500 mg/m$^2$ rituximab and about 70 mg/m$^2$ bendamustine.

In some embodiments, provided methods comprise administering to a patient in need thereof about 250 mg BID Compound 1 and about 375 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 250 mg BID Compound 1, about 375 mg/m$^2$ rituximab and about 70 mg/m$^2$ bendamustine.

In some embodiments, provided methods comprise administering to a patient in need thereof about 250 mg BID Compound 1 and about 500 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 250 mg BID Compound 1, about 500 mg/m$^2$ rituximab and about 70 mg/m$^2$ bendamustine.

In some embodiments, provided methods comprise administering to a patient in need thereof about 375 mg BID Compound 1 and about 375 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 375 mg BID Compound 1, about 375 mg/m$^2$ rituximab and about 70 mg/m$^2$ bendamustine.

In some embodiments, provided methods comprise administering to a patient in need thereof about 375 mg BID Compound 1 and about 500 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 375 mg BID Compound 1, about 500 mg/m$^2$ rituximab and about 70 mg/m$^2$ bendamustine.

In some embodiments, provided methods comprise administering to a patient in need thereof about 500 mg BID Compound 1 and about 375 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 500 mg BID Compound 1, about 375 mg/m$^2$ rituximab and about 70 mg/m$^2$ bendamustine.

In some embodiments, provided methods comprise administering to a patient in need thereof about 500 mg BID Compound 1 and about 500 mg/m$^2$ rituximab. In some such embodiments, provided methods further comprise administering about 25 mg/m$^2$ fludarabine and about 250 mg/m$^2$ cyclophosphamide. In some embodiments, provided methods comprise administering to a patient in need thereof about 500 mg BID Compound 1, about 500 mg/m$^2$ rituximab and about 70 mg/m$^2$ bendamustine.

In some embodiments, rituximab is administered once during a 28-day cycle. In some embodiments, rituximab is administered on cycle 1 day 1 or day 2. In some embodiments, rituximab is administered on day 1 of a 28-day cycle. In some embodiments, rituximab is administered on cycle 2 day 1. In some embodiments, rituximab is administered on cycle 3 day 1. In some embodiments, rituximab is administered on cycle 4 day 1. In some embodiments, rituximab is administered on cycle 5 day 1. In some embodiments, rituximab is administered on cycle 6 day 1. In some embodiments, rituximab is administered on each of cycle 1 day 1 or day 2, cycle 2 day 1, cycle 3 day 1, cycle 4 day 1, cycle 5 day 1 and cycle 6 day 1.

In some embodiments, 375 mg/m$^2$ rituximab is administered on cycle 1 day 1 or day 2, and 500 mg/m$^2$ rituximab is administered on cycle 2 day 1. In some embodiments, 375 mg/m$^2$ rituximab is administered on cycle 1 day 1 or day 2, and 500 mg/m$^2$ rituximab is administered on each of cycle 2 day 1 and cycle 3 day 1. In some embodiments, 375 mg/m$^2$ rituximab is administered on cycle 1 day 1 or day 2, and 500 mg/m$^2$ rituximab is administered on each of cycle 2 day 1, cycle 3 day 1 and cycle 4 day 1. In some embodiments, 375 mg/m$^2$ rituximab is administered on cycle 1 day 1 or day 2, and 500 mg/m$^2$ rituximab is administered on each of cycle 2 day 1, cycle 3 day 1, cycle 4 day 1 and cycle 5 day 1. In some embodiments, 375 mg/m$^2$ rituximab is administered on cycle 1 day 1 or day 2, and 500 mg/m$^2$ rituximab is administered on each of cycle 2 day 1, cycle 3 day 1, cycle 4 day 1, cycle 5 day 1 and cycle 6 day 1.

In some embodiments, 25 mg/m$^2$ fludarabine is administered on days 1-3 of cycles 1, 2, 3, 4, 5 and/or 6. In some embodiments, 250 mg/m$^2$ cyclophosphamide is administered on days 1-3 1 of cycles 1, 2, 3, 4, 5 and/or 6. In some embodiments, 70 mg/m$^2$ bendamustine is administered on days 1 and 2 of cycles 1, 2, 3, 4, 5 and/or 6.

In some embodiments, the combination of Compound 1 and rituximab is administered over a period of 28 consecutive days ("a 28-day cycle"). In some embodiments, the combination of Compound 1 and rituximab is administered for two, three, four, five or six 28-day cycles. In some embodiments, the combination of Compound 1 and rituximab is administered for one, two, three, four, five or six 28-day cycles, and Compound 1 is administered for an additional one, two, three, four, five, six, seven, eight, nine, ten, eleven, twelve, thirteen or fourteen 28-day cycles. In some embodiments, the combination of Compound 1 and rituximab is administered to a patient for one, two, three, four, five or six 28-day cycles, and Compound 1 is administered for the duration of the patient's life. In some embodiments, the combination of Compound 1 and rituximab is administered to a patient for one, two, three, four, five or six 28-day cycles, and either of Compound 1 or rituximab is further administered to the patient for one or more additional 28-day cycles. In some embodiments, the combination of Compound 1 and rituximab is administered to a patient for the duration of the patient's life.

In some embodiments, each of Compound 1, rituximab, fludarabine and cyclophosphamide is administered for one, two, three, four, five or six 28-day cycles, and Compound 1 is administered for an additional one, two, three, four, five, six, seven, eight, nine, ten, eleven, twelve, thirteen or fourteen 28-day cycles.

In some embodiments, each of Compound 1, rituximab and bendamustine is administered for one, two, three, four, five or six 28-day cycles, and Compound 1 is administered for an additional one, two, three, four, five, six, seven, eight, nine, ten, eleven, twelve, thirteen or fourteen 28-day cycles.

In some embodiments, two adjacent 28-day cycles may be separated by a rest period. Such a rest period may be one, two, three, four, five, six, seven or more days during which the patient is not administered either or both Compound 1 and rituximab. In a preferred embodiment, two adjacent 28-day cycles are continuous.

In some embodiments, provided methods comprise administering to a patient in need thereof Compound 1 in combination with rituximab, wherein the patient has failed at least one prior therapy. In some embodiments, provided methods comprise administering to a patient in need thereof each of Compound 1, rituximab, fludarabine and cyclophosphamide, wherein the patient has failed at least one prior therapy. In some embodiments, provided methods comprise administering to a patient in need thereof each of Compound 1, rituximab and bendamustine, wherein the patient has failed at least one prior therapy.

In some embodiments, the present invention provides a system for treating, stabilizing or lessening the severity of one or more diseases or conditions associated with BTK, the system comprising Compound 1 and rituximab. In some embodiments, the system is a kit. In some such embodiments, the kit comprises a pharmaceutical composition comprising Compound 1 and a pharmaceutical composition comprising rituximab.

In some embodiments, the kit comprises twenty-eight (28) daily doses of Compound 1 and one 10 mg/mL vial of rituximab. In some embodiments, the kit comprises twenty-eight (28) daily doses of Compound 1 and one 100 mg/10 mL vial of rituximab. In some embodiments, the kit comprises twenty-eight (28) daily doses of Compound 1 and one 500 mg/50 mL vial of rituximab.

In some embodiments, the kit comprises fifty-six (56) 375 mg doses of Compound 1 and one 10 mg/mL vial of rituximab. In some embodiments, the kit comprises fifty-six (56) 375 mg doses of Compound 1 and one 100 mg/10 mL vial of rituximab. In some embodiments, the kit comprises fifty-six (56) 375 mg doses of Compound 1 and one 500 mg/50 mL vial of rituximab.

In some embodiments, the kit comprises two 375 mg doses of Compound 1 and one 10 mg/mL vial of rituximab. In some embodiments, the kit comprises two 375 mg doses of Compound 1 and one 100 mg/10 mL vial of rituximab. In some embodiments, the kit comprises two 375 mg doses of Compound 1 and one 500 mg/50 mL vial of rituximab. In some embodiments, the kit comprises two 500 mg doses of Compound 1 and one 10 mg/mL dose of rituximab. In some embodiments, the kit comprises two 500 mg doses of Compound 1 and one 100 mg/10 mL vial of rituximab. In some embodiments, the kit comprises two 500 mg doses of Compound 1 and one 500 mg/50 mL vial of rituximab.

IV. Formulations Comprising Compound 1

As described above, provided methods comprise administering to a patient in need thereof a pharmaceutically acceptable composition comprising Compound 1, wherein the pharmaceutically acceptable composition is an oral dosage form. In some embodiments, the pharmaceutically acceptable composition is formulated as a capsule.

In certain embodiments, provided methods comprise administering to a patient in need thereof a pharmaceutically acceptable composition which comprises Compound 1, and one or more pharmaceutically acceptable excipients, such as, for example, binders, film coatings, diluents, disintegrants, surfactants (wetting agents), lubricants and glidants (adsorbents), or combinations thereof. One skilled in the art will readily appreciate that the category under which a particular component is listed is not intended to be limiting; in some cases a particular component might appropriately fit in more than one category. Also, as will be appreciated, the same component can sometimes perform different functions, or can perform more than one function, in the context of a particular formulation, for example depending upon the amount of the ingredient and/or the presence of other ingredients and/or active compound(s). In some embodiments, the pharmaceutically acceptable composition is a blended powder.

i. Binders and Diluents

Pharmaceutical compositions for use in the present invention may comprise one or more binders. Binders are used in the formulation of solid oral dosage forms to hold the active pharmaceutical ingredient and inactive ingredients together in a cohesive mix. In some embodiments, pharmaceutical compositions of the present invention comprise about 5% to about 50% (w/w) of one or more binders and/or diluents. In some embodiments, pharmaceutical compositions of the present invention comprise about 20% (w/w) of one or more binders and/or diluents. Suitable binders and/or diluents (also referred to as "fillers") are known in the art. Representative binders and/or diluents include, but are not limited to, starches such as celluloses (low molecular weight HPC (hydroxypropyl cellulose), microcrystalline cellulose (e.g., Avicel), low molecular weight HPMC (hydroxypropyl methylcellulose), low molecular weight carboxymethyl cellulose, ethylcellulose), sugars such as lactose (i.e. lactose monohydrate), sucrose, dextrose, fructose, maltose, glucose, and polyols such as sorbitol, mannitol, lactitol, malitol and xylitol, or a combination thereof. In some embodiments, a provided composition comprises a binder of microcrystalline cellulose and/or lactose monohydrate.

ii. Disintegrants

Pharmaceutical compositions for use in the present invention may further comprise one or more disintegrants. Suitable disintegrants are known in the art and include, but are not limited to, agar, calcium carbonate, sodium carbonate, sodium bicarbonate, cross-linked sodium carboxymethyl cellulose (croscarmellose sodium), sodium carboxymethyl starch (sodium starch glycolate), microcrystalline cellulose, or a combination thereof. In some embodiments, provided formulations comprise from about 1%, to about 25% disintegrant, based upon total weight of the formulation.

iii. Surfactants

Surfactants, also referred to as bioavailability enhancers, are well known in the art and typically facilitate drug release and absorption by enhancing the solubility of poorly-soluble drugs. Representative surfactants include, but are not limited to, poloxamers, polyoxyethylene ethers, polyoxyethylene fatty acid esters, polyethylene glycol fatty acid esters, polyoxyethylene hydrogenated castor oil, polyoxyethylene alkyl ether, polysorbates, and combinations thereof. In certain embodiments, the surfactant is a poloxamer. In some such embodiments, the poloxamer is poloxamer 407. In some embodiments, compositions for use in the present invention comprise from about 1% to about 30% by weight of surfactant, based upon total weight of the blended powder.

iv. Lubricants

Pharmaceutical compositions of the present invention may further comprise one or more lubricants. Lubricants are agents added in small quantities to formulations to improve certain processing characteristics. Lubricants prevent the formulation mixture from sticking to the compression machinery and enhance product flow by reducing interparticulate friction. Representative lubricants include, but are not limited to, magnesium stearate, glyceryl behenate, sodium stearyl fumarate and fatty acids (i.e. palmitic and stearic acids). In certain embodiments, a lubricant is magnesium stearate. In some embodiments, provided formulations comprise from about 0.2% to about 3% lubricant, based upon total weight of given formulation.

v. Glidants

Pharmaceutical compositions of the present invention may further comprise one or more glidants. Representative glidants include, but are not limited to, silicas (i.e. fumed silica), microcrystalline celluloses, starches (i.e. corn starch) and carbonates (i.e. calcium carbonate and magnesium carbonate). In some embodiments, provided formulations comprise from about 0.2% to about 3% glidant, based upon total weight of given formulation.

vi. N-(3-(5-fluoro-2-(4-(2-methoxyethoxy)phenylamino)pyrimidin-4-ylamino)phenyl)acrylamide besylate As described above, the present invention provides a method of treating a disease or disorder selected from chronic lymphocytic leukemia and small lymphocytic lymphoma, the method comprising administering to a patient in need thereof Compound 1 in combination with rituximab. The besylate salt of Compound 1, N-(3-(5-fluoro-2-(4-(2-methoxyethoxy)phenylamino)pyrimidin-4-ylamino)phenyl) acrylamide benzenesulfonic acid salt, has recently been identified and is currently in clinical trials as monotherapy in subjects with relapsed or refractory B-cell non-Hodgkin's lymphoma (B-NHL), chronic lymphocytic leukemia (CLL) and Waldenstrom's macroglobulinemia (WM). Thus, in some embodiments, provided methods comprise administering to a patient in need thereof a besylate salt of Compound 1.

In some embodiments, provided methods comprise administering to a patient in need thereof a pharmaceutically acceptable composition comprising from about 5% to about 60% of the besylate salt of Compound 1, based upon total weight of the formulation. In some embodiments, provided methods comprise administering to a patient in need thereof a pharmaceutically acceptable composition comprising from about 5% to about 15% or about 7% to about 15% or about 7% to about 10% or about 9% to about 12% of the besylate salt of Compound 1, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of the besylate salt of Compound 1, based upon total weight of the formulation. In certain embodiments, provided methods comprise administering to a patient in need thereof a pharmaceutically acceptable composition comprising from about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of the besylate salt of Compound 1, based upon total weight of given composition or formulation.

In some such embodiments, provided methods comprise administering to a patient in need thereof a pharmaceutical composition comprising a unit dose of Compound 1, wherein Compound 1 is in the form of a besylate salt. In some such embodiments, the unit dose is an amount sufficient to provide about 25 mg, about 50 mg, about 75 mg, about 100 mg, about 125 mg, about 150 mg, about 175 mg, about 200 mg, about 225 mg or about 250 mg of the free base of Compound 1. In some embodiments, the pharmaceutical composition comprising the besylate salt of Compound 1 is a solid oral dosage form.

In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof Compound 1 in combination with rituximab, wherein Compound 1 is administered as the besylate salt. In some such embodiments, the besylate salt of Compound 1 is administered in the form of a composition comprising one or more pharmaceutically acceptable excipients selected from binders, film coatings, diluents, disintegrants, surfactants, lubricants and glidants. In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof each of Compound 1, rituximab, fludarabine and cyclophosphamide, wherein Compound 1 is administered as the besylate salt. In some such embodiments, the besylate salt of Compound 1 is administered in the form of a composition comprising one or more pharmaceutically acceptable excipients selected from binders, film coatings, diluents, disintegrants, surfactants, lubricants and glidants. In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof each of Compound 1, rituximab and bendamustine, wherein Compound 1 is administered as the besylate salt. In some such embodiments, the besylate salt of Compound 1 is administered in the form of a composition comprising one or more pharmaceutically acceptable excipients selected from binders, film coatings, diluents, disintegrants, surfactants, lubricants and glidants.

In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof a pharmaceutical composition comprising the besylate salt of Compound 1 in combination with rituximab, wherein the amount of besylate salt of Compound 1 is sufficient to deliver about 125 mg, about 250 mg, about 325 mg, about 375 mg, about 400 mg, about 500 mg, about 625 mg, about 750 mg, about 1000 mg or about 1250 mg of the free base of Compound 1. In some such embodiments, the pharmaceutical composition further comprises one or more pharmaceutically acceptable excipients selected from binders, film coating, diluents, disintegrants, surfactants, lubricants and glidants. In some such embodiments, the pharmaceutical composition comprises one or more pharmaceutically acceptable excipients selected from microcrystalline cellulose, lactose monohydrate, sodium starch, poloxamer 407, fumed silica and magnesium stearate. In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof a pharmaceutical compositions comprising each of the besylate salt of Compound 1 (i.e., Compound 1 besylate), rituximab, fludarabine and cyclophosphamide, wherein the amount of besylate salt of Compound 1 is sufficient to deliver about 125 mg, about 250 mg, about 325 mg, about 375 mg, about 400 mg, about 500 mg, about 625 mg, about 750 mg, about 1000 mg or about 1250 mg of the free base of Compound 1. In some embodiments, the present invention provides a method of treating, stabilizing or lessening the severity or progression of a disease or disorder selected from the group consisting of chronic lymphocytic leukemia and small lymphocytic lymphoma, the method comprising administering to a patient in need thereof a pharmaceutical compositions comprising each of the besylate salt of Compound 1 (i.e., Compound 1 besylate), rituximab and bendamustine, wherein the amount of besylate salt of Compound 1 is sufficient to deliver about 125 mg, about 250 mg, about 325 mg, about 375 mg, about 400 mg, about 500 mg, about 625 mg, about 750 mg, about 1000 mg or about 1250 mg of the free base of Compound 1.

V. Process for Preparing Pharmaceutical Compositions Comprising Compound 1

Dry Blend Process:

Milled N-(3-(5-fluoro-2-(4-(2-methoxyethoxy)phenylamino)pyrimidin-4-ylamino)phenyl)acrylamide besylate, milled microcrystalline cellulose, milled sodium starch glycolate, milled lactose monohydrate, milled poloxamer 407, and sieved fumed silica are weighed and mechanically blended. An intragranular portion of sieved magnesium stearate (2.0%, per Table 1, below) is added to the blender and the formulation blended. This blended formulation is then roller compacted, milled, and then blended. The blended formulation is additionally roller compacted, milled and then blended. The remainder or extragranular portion of the magnesium stearate (0.5%, per Table 1, below) is added and the final formulation is blended. Capsules are either mechanically filled or manually filled via the flood fill method.

All features of each of the aspects of the invention apply to all other aspects mutatis mutandis. Each of the references referred to herein, including but not limited to patents, patent applications and journal articles, is incorporated by reference herein as though fully set forth in its entirety.

In order that the invention described herein may be more fully understood, the following examples are set forth. It should be understood that these examples are for illustrative purposes only and are not to be construed as limiting this invention in any manner.

EXEMPLIFICATION

Example 1

Dose Escalation Study

N-(3-(5-fluoro-2-(4-(2-methoxyethoxy)phenylamino)pyrimidin-4-ylamino)phenyl)acrylamide besylate is a chemically synthesized small molecule substituted pyrimidine developed as the benzenesulfonic acid salt and is a white to off-white crystalline powder. N-(3-(5-fluoro-2-(4-(2-methoxyethoxy)phenylamino)pyrimidin-4-ylamino)phenyl)acrylamide besylate is an oral, potent ($IC_{50}$<0.5 nM) and selective small molecule inhibitor of Btk. N-(3-(5-fluoro-2-(4-(2-methoxyethoxy)phenylamino)pyrimidin-4-ylamino)phenyl)acrylamide besylate exhibits solubility of approximately 0.16 mg/mL in water and a maximum aqueous solubility of 0.40 mg/mL at approximately pH 3.0. The solubility of N-(3-(5-fluoro-2-(4-(2-methoxyethoxy)phenylamino)pyrimidin-4-ylamino)phenyl)acrylamide besylate in ethanol is approximately 10 mg/mL. N-(3-(5-fluoro-2-(4-(2-methoxyethoxy)phenylamino)pyrimidin-4-ylamino)phenyl)acrylamide besylate exhibits no environmental instabilities (i.e. heat, acid, base) that require special handling.

N-(3-(5-fluoro-2-(4-(2-methoxyethoxy)phenylamino)pyrimidin-4-ylamino)phenyl)acrylamide besylate was formulated into capsules containing the components and quantities listed in Table 1 to obtain the study drug. The capsules listed in Table 1 will be administered during the dose escalation and expansion cohort studies.

TABLE 1

Components of N-(3-(5-fluoro-2-(4-(2-methoxyethoxy)phenylamino)pyrimidin-4-ylamino)phenyl)acrylamide besylate capsules

| Component | Amount per 125 mg Capsule |
|---|---|
| Capsule shell | 1, size 0 white capsule |
| N-(3-(5-fluoro-2-(4-(2-methoxyethoxy)phenylamino)pyrimidin-4-ylamino)phenyl)acrylamide besylate | 174.30 mg (125 mg free base) |
| Microcrystalline cellulose | 101.68 mg |
| Lactose monohydrate | 41.50 mg |
| Sodium starch glycolate | 41.50 mg |
| Poloxamer 407 | 41.50 mg |
| Fumed silica | 4.15 mg |
| Magnesium stearate | 10.38 mg‡ |

‡2.0% (8.30 mg) intragranular; 0.5% (2.08 mg) extragranular.

Rituximab is provided to the physician/investigator in 10 mg/mL vials comprising 100 mg/10 mL or 500 mg/50 mL. Prior to administration, rituximab is diluted to a dose of 1 mg/mL, 2 mg/mL, 3 mg/mL or 4 mg/mL with either 5% dextrose in water or 0.9% sodium chloride. Rituximab is thereafter administered as a 1 mg/mL to 4 mg/mL infusion according to the dosages set forth in Table 2, below.

Study Design

Subjects with relapsed or refractory CLL or SLL who failed at least one prior treatment regimen were enrolled in a "3+3" dose escalation and expansion study to determine the Not Tolerated Dose (NTD), the Optimal Biologic Effect dose (OBE) and the Maximum Tolerated Dose (MTD) of the combination of Compound 1 and rituximab. Approximately 30-42 patients are expected to be enrolled in the study.

Study treatment was administered in 28-day cycles at specified dose levels as scheduled until disease progression, unacceptable toxicity, or discontinuation for any other reason. Subjects will continue on the starting dose until the preliminary recommended Phase 2 dose (RP2D) is determined, at which point they can be switched to the preliminary RP2D.

N-(3-(5-fluoro-2-(4-(2-methoxyethoxy)phenylamino)pyrimidin-4-ylamino)phenyl)acrylamide besylate and rituximab were administered according to the cohorts listed in Table 2:

TABLE 2

Study Dosing Schema for Escalating Dose Portion of Study

| COHORT | N-(3-(5-fluoro-2-(4-(2-methoxyethoxy)phenylamino)pyrimidin-4-ylamino)phenyl) acrylamide besylate | Rituximab |
|---|---|---|
| 1 | 375 mg BID | 6 doses administered as follows: 375 mg/m$^2$ on cycle 1 day 2 500 mg/m$^2$ on cycles 2-6 day 1 |
| 2 | 500 mg BID | |

Within each cohort, subjects were treated PO (oral) BID (daily) with N-(3-(5-fluoro-2-(4-(2-methoxyethoxy)phenylamino)pyrimidin-4-ylamino)phenyl) acrylamide besylate during two initial 28-day treatment cycles and were assessed for safety, tolerability and DLT, as well as pharmacokinetic ("PK"), pharmacodynamic ("PD"), and disease response. In certain instances, the physician-investigator may elect to rest a patient during the study, during which time the patient does not receive treatment. For example, the physician-investigator may elect to rest a patient due to occurrence or recurrence of adverse events. For purposes of clarity, a patient who has been rested is still enrolled in the study until the physician-investigator determines that the patient should not continue treatment, at which time such patients are discontinued from further treatment. In this context, treatment duration refers to the time a patient is enrolled in the study, inclusive of all rest periods, until treatment is discontinued.

Rituximab was administered as a single intravenous (IV) infusion. The initial infusion during cycle 1 was administered at 375 mg/m$^2$; subsequent infusions during cycles 2 through 6 were administered at 500 mg/m$^2$. Administration of rituximab began on day 2 of cycle 1 and on day 1 of each cycle thereafter. Following the cycle 6 infusion, rituximab will be discontinued. Subjects may continue on treatment with N-(3-(5-fluoro-2-(4-(2-methoxyethoxy)phenylamino)pyrimidin-4-ylamino)phenyl)acrylamide besylate if appropriate. The first infusion of rituximab was at a rate of 50 mg/hr. In the absence of infusion toxicity, the infusion rate will be increased by 50 mg/hr increments every 30 minutes, to a maximum of 400 mg/hr. Each subsequent infusion will be initiated at 100 mg/hr. In the absence of infusion toxicity, the infusion rate will be increased by 100 mg/hr increments at 30 minute intervals to a maximum of 400 mg/hr.

The dose level at which a patient is enrolled will be based on which cohort is open at the time of enrollment. Dose escalation, via enrollment in the next higher dose, is allowed only if none (0) of the first three (3) subjects enrolled in any cohort experience dose limiting toxicity (DLT). If one (1) of the first three (3) subjects dosed in any cohort experiences a DLT in cycle 1, three (3) more subjects will be enrolled in that dose cohort. A dose level will be considered to be below the NTD if <1 of 3 DLT evaluable subjects enrolled experiences a DLT during the first 2 cycles. A dose will be considered a NTD when at least two (2) of six (6) DLT-evaluable subjects in that cohort experience a DLT. A MTD will be declared when at least six (6) subjects have been enrolled and safely complete cycle 1 at that dose level. The MTD is defined as the last dose below the NTD with zero (0) or one (1) DLT-evaluable subject experiencing DLT during the first two 28-day cycles.

During the dose escalation phase, a decision to enroll the next higher dose cohort will be based on review of safety and DLT-evaluable patients. The OBE dose is defined as follows:

- a reduction of ≥50% in the size of lymph nodes in ≥ two (2) of six (6) subjects; and/or
- no further increase in exposure with increasing doses; and/or
- a ≥25% increase in lymphocytosis in four (4) of six (6) subjects during the first three 28-day cycles not assessed as progressive disease.

Results.

"Complete Response" (CR) is defined per IWCLL criteria, 2008. (No LN>1.5 cm, no hepatomegaly, splenomegaly, ALC<4000/uL, normocellular marrow<30% lymphocytes, ANC>1500, Platelet Count>100,000 and Hgb>11.0 g/dL). "Partial Response" (PR) was assessed via IWCLL guidelines (at least 2 of the following criteria—lymph node (LN) decrease≥50%; hepatomegaly decrease≥50%; splenomegaly decrease≥50%; ALC decrease≥50%; and at least 1 of the following—platelet count>100,000; ANC>1500/uL or Hgb>11.0 g/dL). A status of PR is the investigator's assessment based on a physical exam evaluation of lymph nodes, spleen and liver and laboratory values of blood counts. Confirmed PR also includes imaging of tumor lesions by CT scan.

Three subjects were enrolled in cohort 1 and treated with N-(3-(5-fluoro-2-(4-(2-methoxyethoxy)phenylamino)pyrimidin-4-ylamino)phenyl) acrylamide besylate in combination with rituximab. Of the three subjects enrolled in cohort 1 on Oct. 16, 2013, one subject is currently in the ninth 28-day cycle and two subjects are currently in the eighth 28-day cycle. Because none of these subjects experienced a DLT during the first 28-day cycle, three subjects were enrolled in cohort 2. Two of the 3 subjects in cohort 2 completed the first two 28 day cycles without a DLT. The third subject has experienced a DLT of grade 3 fatigue and weakness as graded by the NCI-CTCAE guidelines. Three more subjects were enrolled into cohort 2 for further assessment of DLTs and the safety of this dose level.

FIG. 1 summarizes the enrollment and response assessment of patients. All three patients in Cohort 1 have been assessed as having a partial response to study treatment. In all three cases the investigators' assessment of PR as of cycle 3 has been confirmed by CT scans showing a greater than 50% reduction in the size of lymph nodes compared to pre-treatment baseline values. The first subject enrolled is currently being treated in cycle 9 and continues to maintain a partial response. The other two patients in cohorts 1 have continued with treatment into cycle 8 and also maintain a partial response to treatment. Of the six subjects treated in cohort 2, two subjects have achieved a partial response by the start of cycle 3 according to the investigator assessment by examination. One subject has exhibited a partial response by cycle 5 as per investigator assessment. Response assessments for the additional 3 subjects enrolled in cohort 2 is pending.

After full enrollment of each dose escalation cohort and completion of the second cycle of treatment for each dose escalation cohort, the number and type of DLTs and adverse events (AE) occurring during the first two cycles will be evaluated. Subjects will remain on study until the subject discontinues due to disease progression, unacceptable toxicity, withdrawal of consent or any other reason determined by the physician. Preliminary evidence of efficacy will be evaluated.

Expansion Cohorts.

After completion of observation for DLTs in the dose escalation study, the accumulated safety, PK, and PD data will be evaluated to select a preliminary RP2D. The preliminary RP2D will be evaluated in expanded cohorts of 24 subjects or a more complete safety profile and further preliminary evaluation of efficacy. If less than 9 of 24 subjects experience DLTs, then this dose level will be declared the RP2D to be used in further studies. If DLTs are experienced in greater than or equal to 9 of 24 subjects, this dose will be considered to have exceeded the MTD and the previous highest tolerated dose found in the dose escalation cohort of the study will be evaluated in 24 subjects. The dose level will continue to be reduced in a stepwise fashion until less than 9 of 24 subjects experience DLTs.

During the expansion cohort, rituximab will be administered according to the schedule set forth in the dose escalation cohorts. Rituximab will be administered as a single intravenous (IV) infusion. The initial infusion during cycle 1 will be administered at 375 mg/m$^2$; subsequent infusions during cycles 2 through 6 will be administered at 500 mg/m$^2$. Administration of rituximab will begin on day 2 of cycle 1 and on day 1 of each cycle thereafter. Following the cycle 6 infusion, rituximab will be discontinued. Each subject will continue on treatment with N-(3-(5-fluoro-2-(4-(2-methoxyethoxy)phenylamino)pyrimidin-4-ylamino)phenyl)acrylamide besylate until disease progression, unacceptable toxicity or treatment discontinuation for any other reason.

In certain instances, the physician-investigator may elect to rest a patient during the study, during which time the patient does not receive treatment. For example, the physician-investigator may elect to rest a patient due to occurrence or recurrence of adverse events. For purposes of clarity, a patient who has been rested is still enrolled in the study until the physician-investigator determines that the patient should not continue treatment, at which time such patients are discontinued from further treatment. In this context, treatment duration refers to the time a patient is enrolled in the study, inclusive of all rest periods, until treatment is discontinued.

Adverse Events.

For all cohorts, dose limiting toxicities (DLTs) are defined as specified adverse events (AEs) that are observed within the first two 28-day cycles (approximately 56 days) and deemed to be related to treatment. Hematologic DLTs include Grade 4 anemia (hemoglobin decrease) or thrombocytopenia by NCI-CTCAE (v. 4.03) or by IWCLL criteria, whichever results in the lower blood threshold; Grade 4 neutropenia greater than 5 days despite granulocyte colony-stimulating factor (G-CSF) support; and Grade 3 or higher febrile neutropenia. Lymphocytosis may be observed as a consequence of disease progression but has also been described as a redistribution (lymphocytle migration and trafficking) phenomenon in subjects receiving another BTK inhibitor even as lymph node disease responds to treatment. Therefore, lymphocytosis will not be rated for DLT. Reduction of malignant lymphocytosis is an intended therapeutic effect of treatment and will not be considered for DLT.

Non-hematologic DLTs include Grade 4 or higher non-hematologic AEs of any duration; Grade 3 total bilirubin elevation, whether symptomatic or asymptomatic; and any Grade 3 non-hematologic toxicity except nausea, vomiting and diarrhea lasting less than 24 hours following medical therapy; tumor lysis syndrome which does not progress to Grade 4 and resolves in less than 7 days with medical management is not considered a DLT; and transient, and Grade 3 non-hematologic laboratory anomaly that is asymptomatic and rapidly reversible (returns to baseline or ≤Grade 1 within 7 days) will not be considered a DLT.

Subjects without disease progression and without DLT at the end of the first two 28-day treatment cycles are eligible to continue receiving N-(3-(5-fluoro-2-(4-(2-methoxyethoxy)phenylamino)pyrimidin-4-ylamino)phenyl)acrylamide besylate in combination with rituximab for additional 28-day cycles until (i) the patient experiences unacceptable toxicity, (ii) the underlying malignancy progresses, (iii) the patient withdraws consent, or (iv) the treating physician-investigator otherwise determines that the patient should not continue treatment. Subjects experiencing a DLT may remain on study treatment if the treating investigator determines that the subject is receiving a clinical benefit from the study treatment. Rituximab will only be administered for the first 6 cycles; however patients continuing to benefit from N-(3-(5-fluoro-2-(4-(2-methoxyethoxy)phenylamino)pyrimidin-4-ylamino)phenyl)acrylamide besylate can remain on treatment.

One subject in cohort 1 experienced herpetic esophagitis during cycle 2 and two SAEs during cycle 5; an incidence of atrial fibrillation and pneumonia and an incidence of hypotension, altered mental status and pneumonia, both reports which were considered unrelated to the study drugs. All 3 of these SAE reports required brief hospitalizations and drug interruptions, however following re-challenged with drug this subject has subsequently achieved further improvement in disease status. In cohort 2, one subject experienced scrotal abscess during cycle 2, which was deemed unrelated to the study drugs. Another cohort 2 subject experienced a Grade 3 fatigue during cycle 2 which was declared a DLT; however, the AE was not reported as serious. This patient remains on study treatment at a reduced dose of N-(3-(5-fluoro-2-(4-(2-methoxyethoxy)phenylamino)pyrimidin-4-ylamino)phenyl)acrylamide besylate. One additional subject in cohort 2 experienced visual disturbance during cycle 2, which was present at baseline. Two subjects, one from each cohort, reported Grade 3 neutropenia.

Example 2

One particular irreversible BTK inhibitor, Compound 2, was screened against 342 kinases to ascertain kinase activity and/or selectivity:

Compound 2

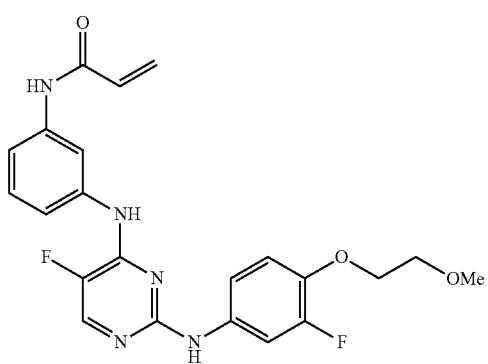

The binding assay system for profiling kinase activity were based upon HotSpot technology (Reaction Biology Corp.; Malvern, Pa., USA) and utilized radio-isotope-based P81 filtration. Compound 2 was dissolved in pure DMSO to make a 10 mM stock solution and serial dilutions were performed to a final 3 μM test concentration. Substrates for the various kinases tested against Compound 2 (substrate information available on the Reaction Biology Corp. website) were prepared fresh daily in Reaction Buffer. Any required cofactors were then added to the substrate solution. The identification and selection of the appropriate cofactor for each kinase is within the ability of a person skilled in the art. See, for example, *Handbook of Assay Development in Drug Discovery*, Ed. Lisa K. Minor, 2006: CRC Press, Boca Raton, Fla.; Gao et al., "A broad activity screen in support of a chemogenomic map for kinase signalling research and drug discovery," *Biochem J.* 2013, 451(2): 313-28; and Eglen et al., "Drug discovery and the human kinome: Recent trends," *Pharmacology & Therapeutics* 2011, 130(2): 144-156. The kinase was then added to the substrate solution and gently mixed. Compound 2 (5 nL) was then added to the kinase reaction mixture by acoustical droplet ejection and preincubated for 30 min at room temperature. $^{33}$P-ATP (100 μM) was delivered into the reaction mixture to initiate the reaction. This was followed by incubation at room temperature for 2 h. The reaction was terminated and any unreacted phosphate was washed away using 0.1% phosphoric acid prior to detection utilizing a proprietary technology. The study was performed in duplicate and staurosporine, a non-selective, ATP-competitive kinase inhibitor, was used a the positive control in a 10-dose IC50 mode with 3-fold serial dilutions starting at 1 μM, 50 μM or 100 μM. DMSO was used as the negative control.

Determination of Percent Inhibition.

Percent inhibition of a kinase by a test compound, e.g., Compound 2, was determined according to the following formula: percent inhibition=[(kinase activity of negative control)−(kinase activity in presence of a test compound, e.g., Compound 2)/(kinase activity of negative control)]× 100. Percent inhibition was expressed as an average where the assay was performed more than once, e.g., in duplicate.

Table 3 sets forth the average percent inhibition for Compound 2 against various kinases:

TABLE 3

Average Percent Inhibition of Kinases by Compound 2

| Kinase | % Enzyme Activity (relative to DMSO controls) | | Average % Inhibition |
|---|---|---|---|
| | Run 1 | Run 2 | |
| ABL1 | 45.37 | 45.23 | 54.70 |
| ABL2/ARG | 37.26 | 37.07 | 62.84 |
| ACK1 | 22.59 | 22.50 | 77.46 |
| AKT1 | 95.13 | 93.13 | 5.87 |
| AKT2 | 93.65 | 97.89 | 4.23 |
| AKT3 | 110.81 | 102.89 | −6.85 |
| ALK | 82.52 | 83.61 | 16.94 |
| ALK1/ACVRL1 | 124.78 | 123.91 | −24.35 |
| ALK2/ACVR1 | 385.44 | 385.47 | −285.46 |
| ALK3/BMPR1A | 104.30 | 104.51 | −4.41 |
| ALK4/ACVR1B | 140.52 | 143.80 | −42.16 |
| ALK5/TGFBR1 | 106.06 | 110.00 | −8.03 |
| ALK6/BMPR1B | 176.94 | 183.87 | −80.41 |
| ARAF | 102.92 | 100.02 | −1.47 |
| ARK5/NUAK1 | 13.26 | 13.31 | 86.72 |
| ASK1/MAP3K5 | 100.91 | 102.32 | −1.62 |
| Aurora A | 12.26 | 11.03 | 88.35 |
| Aurora B | 13.18 | 12.94 | 86.94 |
| Aurora C | 26.24 | 29.79 | 71.98 |

TABLE 3-continued

Average Percent Inhibition of Kinases by Compound 2

| Kinase | % Enzyme Activity (relative to DMSO controls) Run 1 | Run 2 | Average % Inhibition |
|---|---|---|---|
| AXL | 48.58 | 48.79 | 51.31 |
| BLK | 6.30 | 6.37 | 93.66 |
| BMPR2 | 83.77 | 83.85 | 16.19 |
| BMX/ETK | 0.93 | 1.23 | 98.92 |
| BRAF | 100.83 | 99.10 | 0.04 |
| BRK | 25.10 | 24.97 | 74.96 |
| BRSK1 | 87.10 | 89.40 | 11.75 |
| BRSK2 | 90.99 | 91.69 | 8.66 |
| BTK | 3.69 | 5.40 | 95.45 |
| CAMK1a | 109.10 | 111.65 | −10.38 |
| CAMK1b | 103.91 | 104.95 | −4.43 |
| CAMK1d | 103.60 | 103.13 | −3.36 |
| CAMK1g | 99.95 | 101.49 | −0.72 |
| CAMK2a | 109.14 | 110.06 | −9.60 |
| CAMK2b | 96.40 | 95.81 | 3.89 |
| CAMK2d | 123.75 | 122.81 | −23.28 |
| CAMK2g | 103.51 | 110.85 | −7.18 |
| CAMK4 | 102.16 | 102.35 | −2.26 |
| CAMKK1 | 93.48 | 87.89 | 9.31 |
| CAMKK2 | 74.65 | 71.82 | 26.77 |
| CDC7/DBF4 | 100.26 | 103.78 | −2.02 |
| CDK1/cyclin A | 111.93 | 124.07 | −18.00 |
| CDK1/cyclin B | 87.16 | 87.03 | 12.91 |
| CDK1/cyclin E | 100.38 | 102.23 | −1.30 |
| CDK16/cyclin Y | 104.10 | 103.36 | −3.73 |
| CDK2/cyclin A | 85.83 | 86.86 | 13.66 |
| CDK2/cyclin A1 | 78.25 | 77.74 | 22.00 |
| CDK2/cyclin E | 87.92 | 92.03 | 10.02 |
| CDK3/cyclin E | 78.15 | 76.95 | 22.45 |
| CDK4/cyclin D1 | 95.58 | 96.28 | 4.07 |
| CDK4/cyclin D3 | 95.54 | 94.15 | 5.15 |
| CDK5/p25 | 89.55 | 92.26 | 9.10 |
| CDK5/p35 | 94.97 | 96.06 | 4.49 |
| CDK6/cyclin D1 | 101.41 | 100.42 | −0.92 |
| CDK6/cyclin D3 | 99.55 | 100.13 | 0.16 |
| CDK7/cyclin H | 98.10 | 97.18 | 2.36 |
| CDK9/cyclin K | 81.70 | 82.16 | 18.07 |
| CDK9/cyclin T1 | 87.76 | 91.54 | 10.35 |
| CHK1 | 93.14 | 94.56 | 6.15 |
| CHK2 | 25.85 | 25.28 | 74.43 |
| CK1a1 | 107.76 | 105.57 | −6.67 |
| CK1d | 99.87 | 100.20 | −0.03 |
| CK1epsilon | 101.51 | 102.41 | −1.96 |
| CK1g1 | 88.77 | 90.27 | 10.48 |
| CK1g2 | 89.13 | 85.74 | 12.57 |
| CK1g3 | 84.15 | 85.84 | 15.01 |
| CK2a | 117.05 | 123.24 | −20.15 |
| CK2a2 | 98.25 | 105.38 | −1.81 |
| c-Kit | 77.47 | 79.45 | 21.54 |
| CLK1 | 74.39 | 77.44 | 24.08 |
| CLK2 | 50.21 | 50.65 | 49.57 |
| CLK3 | 90.36 | 95.83 | 6.90 |
| CLK4 | 57.40 | 53.92 | 44.34 |
| c-MER | 66.48 | 66.40 | 33.56 |
| c-MET | 102.62 | 100.36 | −1.49 |
| COT1/MAP3K8 | 101.72 | 100.94 | −1.33 |
| CSK | 81.71 | 81.81 | 18.24 |
| c-Src | 28.17 | 27.88 | 71.97 |
| CTK/MATK | 102.20 | 103.87 | −3.03 |
| DAPK1 | 102.79 | 93.48 | 1.86 |
| DAPK2 | 108.05 | 111.72 | −9.89 |
| DCAMKL1 | 98.43 | 97.52 | 2.02 |
| DCAMKL2 | 100.15 | 99.50 | 0.18 |
| DDR1 | 25.70 | 24.12 | 75.09 |
| DDR2 | 102.90 | 104.85 | −3.87 |
| DLK/MAP3K12 | 74.17 | 80.18 | 22.82 |
| DMPK | 104.46 | 102.05 | −3.25 |
| DMPK2 | 97.36 | 99.56 | 1.54 |
| DRAK1/STK17A | 82.93 | 80.57 | 18.25 |
| DYRK1/DYRK1A | 87.66 | 88.41 | 11.96 |
| DYRK1B | 78.60 | 80.92 | 20.24 |
| DYRK2 | 60.98 | 62.12 | 38.45 |
| DYRK3 | 85.99 | 85.89 | 14.06 |
| DYRK4 | 105.18 | 105.53 | −5.35 |
| EGFR | 19.23 | 20.17 | 80.30 |
| EPHA1 | 99.47 | 101.01 | −0.24 |
| EPHA2 | 84.23 | 84.12 | 15.82 |
| EPHA3 | 96.21 | 100.18 | 1.81 |
| EPHA4 | 92.86 | 88.96 | 9.09 |
| EPHA5 | 89.11 | 93.57 | 8.66 |
| EPHA6 | 95.52 | 102.01 | 1.24 |
| EPHA7 | 60.01 | 64.14 | 37.93 |
| EPHA8 | 94.25 | 93.79 | 5.98 |
| EPHB1 | 79.45 | 79.66 | 20.44 |
| EPHB2 | 104.27 | 106.64 | −5.45 |
| EPHB3 | 99.17 | 98.21 | 1.31 |
| EPHB4 | 81.25 | 81.45 | 18.65 |
| ERBB2/HER2 | 39.81 | 37.50 | 61.34 |
| ERBB4/HER4 | 9.15 | 8.32 | 91.27 |
| ERK1 | 97.44 | 99.93 | 1.32 |
| ERK2/MAPK1 | 105.72 | 102.79 | −4.25 |
| ERK5/MAPK7 | 100.83 | 99.91 | −0.37 |
| ERK7/MAPK15 | 63.77 | 66.05 | 35.09 |
| FAK/PTK2 | 62.84 | 62.86 | 37.15 |
| FER | 88.07 | 88.26 | 11.83 |
| FES/FPS | 63.95 | 65.95 | 35.05 |
| FGFR1 | 41.38 | 39.31 | 59.66 |
| FGFR2 | 37.28 | 35.97 | 63.37 |
| FGFR3 | 32.14 | 31.78 | 68.04 |
| FGFR4 | 66.32 | 63.44 | 35.12 |
| FGR | 39.73 | 40.47 | 59.90 |
| FLT1/VEGFR1 | 83.62 | 79.20 | 18.59 |
| FLT3 | 3.19 | 3.25 | 96.78 |
| FLT4/VEGFR3 | 43.82 | 44.24 | 55.97 |
| FMS | 64.50 | 67.34 | 34.08 |
| FRK/PTK5 | 100.54 | 97.96 | 0.75 |
| FYN | 81.08 | 81.84 | 18.54 |
| GCK/MAP4K2 | 100.27 | 100.02 | −0.14 |
| GLK/MAP4K3 | 102.03 | 108.13 | −5.08 |
| GRK1 | 103.55 | 103.40 | −3.47 |
| GRK2 | 104.15 | 103.91 | −4.03 |
| GRK3 | 99.45 | 100.95 | −0.20 |
| GRK4 | 107.15 | 106.07 | −6.61 |
| GRK5 | 103.03 | 102.15 | −2.59 |
| GRK6 | 102.34 | 103.73 | −3.03 |
| GRK7 | 89.14 | 90.93 | 9.96 |
| GSK3a | 75.97 | 74.98 | 24.53 |
| GSK3b | 121.82 | 122.56 | −22.19 |
| Haspin | 90.56 | 89.91 | 9.77 |
| HCK | 71.99 | 68.97 | 29.52 |
| HGK/MAP4K4 | 98.87 | 98.60 | 1.27 |
| HIPK1 | 87.63 | 91.73 | 10.32 |
| HIPK2 | 95.75 | 98.61 | 2.82 |
| HIPK3 | 112.11 | 118.15 | −15.13 |
| HIPK4 | 93.61 | 93.78 | 6.31 |
| HPK1/MAP4K1 | 85.77 | 88.42 | 12.90 |
| IGF1R | 82.83 | 85.99 | 15.59 |
| IKKa/CHUK | 91.43 | 91.50 | 8.54 |
| IKKb/IKBKB | 95.44 | 97.06 | 3.75 |
| IKKe/IKBKE | 78.26 | 78.18 | 21.78 |
| IR | 84.52 | 84.68 | 15.40 |
| IRAK1 | 76.49 | 74.41 | 24.55 |
| IRAK4 | 88.61 | 86.52 | 12.43 |
| IRR/INSRR | 88.90 | 90.97 | 10.07 |
| ITK | 7.97 | 7.95 | 92.04 |
| JAK1 | 59.70 | 59.03 | 40.63 |
| JAK2 | 108.64 | 114.63 | −11.63 |
| JAK3 | 2.53 | 2.73 | 97.37 |
| JNK1 | 88.14 | 87.66 | 12.10 |
| JNK2 | 92.48 | 95.08 | 6.22 |
| JNK3 | 110.08 | 115.56 | −12.82 |
| KDR/VEGFR2 | 83.35 | 81.24 | 17.70 |
| KHS/MAP4K5 | 94.89 | 90.82 | 7.15 |
| LATS1 | 89.52 | 89.80 | 10.34 |

TABLE 3-continued

Average Percent Inhibition of Kinases by Compound 2

| Kinase | % Enzyme Activity (relative to DMSO controls) Run 1 | Run 2 | Average % Inhibition |
|---|---|---|---|
| LATS2 | 88.40 | 91.16 | 10.22 |
| LCK | 64.67 | 63.36 | 35.99 |
| LCK2/ICK | 100.94 | 95.10 | 1.98 |
| LIMK1 | 60.98 | 61.36 | 38.83 |
| LIMK2 | 101.00 | 100.73 | −0.86 |
| LKB1 | 99.24 | 95.94 | 2.41 |
| LOK/STK10 | 43.10 | 43.01 | 56.94 |
| LRRK2 | 33.02 | 35.12 | 65.93 |
| LYN | 71.67 | 73.24 | 27.54 |
| LYN B | 92.90 | 95.69 | 5.70 |
| MAPKAPK2 | 109.81 | 105.91 | −7.86 |
| MAPKAPK3 | 102.28 | 102.63 | −2.45 |
| MAPKAPK5/PRAK | 109.84 | 113.33 | −11.58 |
| MARK1 | 90.93 | 97.35 | 5.86 |
| MARK2/PAR-1Ba | 99.58 | 97.83 | 1.30 |
| MARK3 | 101.48 | 100.37 | −0.92 |
| MARK4 | 82.17 | 80.87 | 18.48 |
| MEK1 | 109.05 | 111.60 | −10.33 |
| MEK2 | 106.36 | 104.95 | −5.66 |
| MEK3 | 117.30 | 113.34 | −15.32 |
| MEKK1 | 112.92 | 116.55 | −14.74 |
| MEKK2 | 108.13 | 113.65 | −10.89 |
| MEKK3 | 101.68 | 106.39 | −4.03 |
| MELK | 108.80 | 107.34 | −8.07 |
| MINK/MINK1 | 100.72 | 97.49 | 0.90 |
| MKK4 | 116.84 | 116.35 | −16.60 |
| MKK6 | 96.36 | 97.41 | 3.11 |
| MLCK/MYLK | 95.57 | 95.24 | 4.59 |
| MLCK2/MYLK2 | 71.62 | 68.13 | 30.13 |
| MLK1/MAP3K9 | 14.50 | 14.05 | 85.72 |
| MLK2/MAP3K10 | 45.39 | 45.33 | 54.64 |
| MLK3/MAP3K11 | 27.89 | 25.23 | 73.44 |
| MNK1 | 97.78 | 94.26 | 3.98 |
| MNK2 | 83.04 | 83.21 | 16.88 |
| MRCKa/CDC42BPA | 113.51 | 115.15 | −14.33 |
| MRCKb/CDC42BPB | 106.78 | 105.47 | −6.12 |
| MSK1/RPS6KA5 | 94.87 | 99.72 | 2.70 |
| MSK2/RPS6KA4 | 103.35 | 97.38 | −0.36 |
| MSSK1/STK23 | 108.42 | 104.81 | −6.62 |
| MST1/STK4 | 70.20 | 68.65 | 30.58 |
| MST2/STK3 | 91.08 | 88.64 | 10.14 |
| MST3/STK24 | 86.56 | 84.46 | 14.49 |
| MST4 | 97.85 | 104.33 | −1.09 |
| MUSK | 70.16 | 68.05 | 30.89 |
| MYLK3 | 113.48 | 116.49 | −14.98 |
| MYO3b | 103.52 | 101.67 | −2.59 |
| NEK1 | 52.74 | 53.95 | 46.65 |
| NEK11 | 92.53 | 92.84 | 7.32 |
| NEK2 | 102.22 | 106.65 | −4.44 |
| NEK3 | 76.65 | 75.11 | 24.12 |
| NEK4 | 84.64 | 88.33 | 13.52 |
| NEK5 | 60.25 | 60.87 | 39.44 |
| NEK6 | 105.95 | 105.43 | −5.69 |
| NEK7 | 98.29 | 100.34 | 0.68 |
| NEK9 | 83.83 | 84.30 | 15.94 |
| NLK | 99.61 | 102.97 | −1.29 |
| OSR1/OXSR1 | 116.94 | 121.56 | −19.25 |
| P38a/MAPK14 | 105.80 | 107.56 | −6.68 |
| P38b/MAPK11 | 101.64 | 101.17 | −1.41 |
| P38d/MAPK13 | 98.94 | 99.78 | 0.64 |
| P38g | 105.35 | 105.71 | −5.53 |
| P70S6K/RPS6KB1 | 85.89 | 81.02 | 16.54 |
| P70S6Kb/RPS6KB2 | 95.60 | 96.10 | 4.15 |
| PAK1 | 96.27 | 98.58 | 2.58 |
| PAK2 | 95.53 | 94.87 | 4.80 |
| PAK3 | 91.86 | 95.22 | 6.46 |
| PAK4 | 98.70 | 96.40 | 2.45 |
| PAK5 | 122.54 | 132.33 | −27.43 |
| PAK6 | 79.30 | 84.76 | 17.97 |
| PASK | 94.65 | 93.08 | 6.14 |
| PBK/TOPK | 98.58 | 95.27 | 3.07 |
| PDGFRa | 63.93 | 62.78 | 36.65 |
| PDGFRb | 47.74 | 47.41 | 52.42 |
| PDK1/PDPK1 | 106.60 | 105.33 | −5.96 |
| PHKg1 | 85.80 | 85.18 | 14.51 |
| PHKg2 | 117.59 | 111.88 | −14.73 |
| PIM1 | 103.69 | 103.94 | −3.82 |
| PIM2 | 135.59 | 129.41 | −32.50 |
| PIM3 | 103.69 | 99.97 | −1.83 |
| PKA | 85.81 | 85.13 | 14.53 |
| PKAcb | 49.70 | 51.07 | 49.62 |
| PKAcg | 127.92 | 127.73 | −27.82 |
| PKCa | 88.40 | 88.80 | 11.40 |
| PKCb1 | 72.71 | 72.06 | 27.62 |
| PKCb2 | 50.13 | 48.85 | 50.51 |
| PKCd | 100.41 | 96.02 | 1.78 |
| PKCepsilon | 93.22 | 94.21 | 6.29 |
| PKCeta | 108.82 | 116.79 | −12.81 |
| PKCg | 83.88 | 84.16 | 15.98 |
| PKCiota | 105.24 | 105.70 | −5.47 |
| PKCmu/PRKD1 | 74.85 | 75.85 | 24.65 |
| PKCnu/PRKD3 | 80.06 | 79.79 | 20.07 |
| PKCtheta | 83.65 | 84.12 | 16.12 |
| PKCzeta | 99.81 | 95.15 | 2.52 |
| PKD2/PRKD2 | 86.37 | 86.22 | 13.70 |
| PKG1a | 87.99 | 94.55 | 8.73 |
| PKG1b | 85.36 | 87.08 | 13.78 |
| PKG2/PRKG2 | 87.22 | 84.45 | 14.16 |
| PKN1/PRK1 | 93.83 | 92.30 | 6.94 |
| PKN2/PRK2 | 93.30 | 91.42 | 7.64 |
| PKN3/PRK3 | 106.24 | 108.40 | −7.32 |
| PLK1 | 91.11 | 92.77 | 8.06 |
| PLK2 | 86.63 | 86.74 | 13.32 |
| PLK3 | 96.95 | 100.49 | 1.28 |
| PLK4/SAK | 54.75 | 55.16 | 45.04 |
| PRKX | 97.87 | 98.53 | 1.80 |
| PYK2 | 70.59 | 70.13 | 29.64 |
| RAF1 | 83.34 | 83.62 | 16.52 |
| RET | 13.17 | 13.63 | 86.60 |
| RIPK2 | 77.59 | 75.01 | 23.70 |
| RIPK3 | 116.80 | 120.69 | −18.75 |
| RIPK5 | 96.13 | 99.22 | 2.32 |
| ROCK1 | 107.64 | 105.14 | −6.39 |
| ROCK2 | 102.29 | 101.47 | −1.88 |
| RON/MST1R | 103.11 | 101.37 | −2.24 |
| ROS/ROS1 | 13.52 | 13.26 | 86.61 |
| RSK1 | 73.29 | 72.45 | 27.13 |
| RSK2 | 82.57 | 84.26 | 16.59 |
| RSK3 | 85.80 | 85.16 | 14.52 |
| RSK4 | 77.21 | 77.21 | 22.79 |
| SGK1 | 99.71 | 99.55 | 0.37 |
| SGK2 | 71.38 | 76.59 | 26.02 |
| SGK3/SGKL | 99.54 | 105.31 | −2.42 |
| SIK1 | 48.40 | 48.72 | 51.44 |
| SIK2 | 56.26 | 57.07 | 43.34 |
| SIK3 | 91.33 | 92.80 | 7.93 |
| SLK/STK2 | 74.89 | 75.27 | 24.92 |
| SNARK/NUAK2 | 83.70 | 84.92 | 15.69 |
| SRMS | 123.69 | 122.52 | −23.11 |
| SRPK1 | 98.81 | 96.73 | 2.23 |
| SRPK2 | 90.92 | 89.61 | 9.73 |
| SSTK/TSSK6 | 107.37 | 99.84 | −3.60 |
| STK16 | 22.93 | 21.04 | 78.01 |
| STK22D/TSSK1 | 88.04 | 89.72 | 11.12 |
| STK25/YSK1 | 94.47 | 94.10 | 5.72 |
| STK32B/YANK2 | 95.81 | 93.60 | 5.30 |
| STK32C/YANK3 | 104.94 | 107.08 | −6.01 |
| STK33 | 51.19 | 52.54 | 48.14 |
| STK38/NDR1 | 92.71 | 93.70 | 6.79 |
| STK38L/NDR2 | 106.68 | 95.97 | −1.33 |
| STK39/STLK3 | 91.63 | 92.89 | 7.74 |
| SYK | 78.04 | 77.10 | 22.43 |
| TAK1 | 73.39 | 71.98 | 27.32 |
| TAOK1 | 100.50 | 96.25 | 1.63 |

TABLE 3-continued

Average Percent Inhibition of Kinases by Compound 2

| Kinase | % Enzyme Activity (relative to DMSO controls) Run 1 | Run 2 | Average % Inhibition |
|---|---|---|---|
| TAOK2/TAO1 | 98.49 | 94.44 | 3.53 |
| TAOK3/JIK | 94.52 | 90.00 | 7.74 |
| TBK1 | 58.13 | 59.19 | 41.34 |
| TEC | 10.36 | 11.47 | 89.08 |
| TESK1 | 97.22 | 98.52 | 2.13 |
| TGFBR2 | 98.07 | 102.31 | −0.19 |
| TIE2/TEK | 102.88 | 107.55 | −5.21 |
| TLK1 | 102.43 | 103.40 | −2.91 |
| TLK2 | 107.74 | 104.89 | −6.32 |
| TNIK | 66.84 | 67.77 | 32.69 |
| TNK1 | 15.91 | 16.61 | 83.74 |
| TRKA | 117.40 | 117.94 | −17.67 |
| TRKB | 86.53 | 85.00 | 14.24 |
| TRKC | 35.08 | 32.34 | 66.29 |
| TSSK2 | 97.01 | 96.27 | 3.36 |
| TSSK3/STK22C | 132.55 | 132.59 | −32.57 |
| TTBK1 | 101.11 | 102.19 | −1.65 |
| TTBK2 | 102.05 | 99.67 | −0.86 |
| TXK | 0.42 | 0.03 | 99.77 |
| TYK1/LTK | 77.75 | 75.81 | 23.22 |
| TYK2 | 48.20 | 46.63 | 52.58 |
| TYRO3/SKY | 95.11 | 96.84 | 4.03 |
| ULK1 | 100.12 | 101.06 | −0.59 |
| ULK2 | 102.27 | 109.21 | −5.74 |
| ULK3 | 79.58 | 76.98 | 21.72 |
| VRK1 | 84.28 | 89.86 | 12.93 |
| VRK2 | 94.00 | 95.88 | 5.06 |
| WEE1 | 73.06 | 74.89 | 26.03 |
| WNK1 | 112.15 | 112.04 | −12.10 |
| WNK2 | 92.35 | 95.28 | 6.19 |
| WNK3 | 91.35 | 91.97 | 8.34 |
| YES/YES1 | 18.72 | 18.27 | 81.50 |
| ZAK/MLTK | 83.71 | 85.00 | 15.65 |
| ZAP70 | 110.35 | 108.07 | −9.21 |
| ZIPK/DAPK3 | 109.39 | 113.13 | −11.26 |

Example 3

Capsules comprising N-(3-(5-fluoro-2-(4-(2-methoxyethoxy)phenylamino)pyrimidin-4-ylamino)phenyl)acrylamide besylate (Compound 1 besylate) for use in this study correspond to Table 1 in Example 1.

Rituximab is provided to the physician/investigator in 10 mg/mL vials comprising 100 mg/10 mL or 500 mg/50 mL. Prior to administration, rituximab is diluted to a dose of 1 mg/mL, 2 mg/mL, 3 mg/mL or 4 mg/mL with either 5% dextrose in water or 0.9% sodium chloride. Rituximab is thereafter administered as a 1 mg/mL to 4 mg/mL infusion according to the dosages set forth in Table 4, below.

Fludarabine is approved as Fludara® and is commercially available in a vial containing a sterile lyophilized solid cake which contains 50 mg of fludarabine phosphate, 50 mg of mannitol, and sodium hydroxide. The solid cake is reconstituted with 2 mL of Sterile Water for Injection USP, resulting in a 25 mg/mL solution.

Cyclophosphamide is approved as Cytoxan® and is commerically available as a sterile powder which con be reconstituted according to the package insert.

Bendamustine is approved as Treanda® and is commercially available as a single-use vial containing 100 mg of bendamustine hydrochloride as a lyophilized powder. The powder is reconstituted with 20 mL of Sterile Water for Injection USP, resulting in a 5 mg/mL solution, which is further diluted with 0.9% Sodium Chloride Injection, USP or 2.5% Dextrose/0.45% Sodium Chloride Injection, USP immediately prior to injection (final concentration of 0.2-0.6 mg/mL).

Study Design

Subjects with relapsed or refractory CLL or SLL who failed at least one prior treatment regimen will be enrolled in a "3+3" dose escalation and expansion study to determine the Not Tolerated Dose (NTD), the Optimal Biologic Effect dose (OBE) and the Maximum Tolerated Dose (MTD) of Compound 1, rituximab, fludarabine and cyclophosphamide (Arm A) and Compound 1, rituximab and bendamustine (Arm B). Approximately 30-42 patients are expected to be enrolled in the study.

Study treatment will be administered in 28-day cycles at specified dose levels as scheduled until disease progression, unacceptable toxicity, or discontinuation for any other reason. Subjects will continue on the starting dose until the preliminary recommended Phase 2 dose (RP2D) is determined, at which point they can be switched to the preliminary RP2D.

Compound 1 besylate, rituximab, fludarabine and cyclophosphamide will be administered according to the cohorts for Arm A of the study, listed in Table 4:

TABLE 4

Study Dosing Schema for Arm A Escalating Dose Portion of Study

| COHORT | Compound 1 besylate | Rituximab | Fludarabine | Cyclophosphamide |
|---|---|---|---|---|
| 1A | 375 mg BID: days 8-28 for cycle 1 days 1-28 for subsequent cycles | 6 doses administered as follows: 375 mg/m² on day 1 for cycle 1 500 mg/m² on day 1 for cycles 2-6 | 18 doses administered as follows: 25 mg/m² on days 1-3 for cycles 1-6 | 18 doses administered as follows: 250 mg/m² on days 1-3 for cycles 1-6 |
| 2A | 500 mg BID: days 8-28 for cycle 1 days 1-28 for subsequent cycles | | | |

Compound 1 besylate, rituximab and bendamustine will be administered according to the cohorts for Arm B of the study, listed in Table 5:

TABLE 5

Study Dosing Schema for Arm B Escalating Dose Portion of Study

| COHORT | Compound 1 besylate | Rituximab | Bendamustine |
|---|---|---|---|
| 1B | 375 mg BID: days 8-28 for cycle 1 days 1-28 for subsequent cycles | 6 doses administered as follows: 375 mg/m² on day 1 for cycle 1 500 mg/m² on day 1 for cycles 2-6 | 12 doses administered as follows: 70 mg/m² on days 1-2 for cycles 1-6 |
| 2B | 500 mg BID: days 8-28 for cycle 1 days 1-28 for subsequent cycles | | |

Within each cohort, subjects will be treated PO (oral) BID (daily) with Compound 1 besylate according to Tables 4 or 5 during two initial 28-day treatment cycles and will be assessed for safety, tolerability and DLT, as well as pharmacokinetic ("PK"), pharmacodynamic ("PD"), and disease response.

Rituximab will be administered as a single intravenous (IV) infusion. The initial infusion during cycle 1 will be administered at 375 mg/m$^2$; subsequent infusions during cycles 2 through 6 will be administered at 500 mg/m$^2$. Administration of rituximab will begin on day 1 of cycle 1 and on day 1 of each cycle thereafter. Following the cycle 6 infusion, rituximab will be discontinued. Subjects may continue on treatment with Compound 1 besylate if appropriate. The first infusion of rituximab will be at a rate of 50 mg/hr. In the absence of infusion toxicity, the infusion rate will be increased by 50 mg/hr increments every 30 minutes, to a maximum of 400 mg/hr. Each subsequent infusion will be initiated at 100 mg/hr. In the absence of infusion toxicity, the infusion rate will be increased by 100 mg/hr increments at 30 minute intervals to a maximum of 400 mg/hr.

Fludarabine will be administered as a 25 mg/mL (Sterile Water USP) intravenous infusion of 25 mg/m$^2$ over 20-30 minutes on days 1-3 for cycles 1-6. Cyclophosphamide will be administered as a 100 mg/5 mL intravenous infusion of 250 mg/m$^2$ over 10-30 minutes on days 1-3 for cycles 1-6.

Bendamustine will be diluted to 5 mg/mL concentration with Sterile Water for Injection. Immediately prior to use, the bendamustine solution will be transferred to a 500 mL infusion bag of 0.9% Sodium Chloride Injection USP. The bendamustine infusion solution will then be administered as an intravenous infusion of 70 mg/m$^2$ over 30-60 minutes on days 1 and 2 for cycles 1-6.

Example 4

Capsules comprising N-(3-(5-fluoro-2-(4-(2-methoxyethoxy)phenylamino)pyrimidin-4-ylamino)phenyl)acrylamide besylate (Compound 1 besylate) for use in this study correspond to Table 1 in Example 1.

Prior to administration, each dose of ofatumumab is prepared in 1000 mL 0.9% Sodium Chloride Injection, USP solutions. The dilution of ofatumumab is as follows:
  300 mg dose: 5 mL from each of 3 single use 100 mg vials is added to 985 mL of 0.9% Sodium Chloride Injection, USP.
  2000 mg dose: 50 mL from each of 2 single use 1000 mg vials is added to 900 mL of 0.9% Sodium Chloride Injection, USP.

Study Design

Subjects with relapsed or refractory CLL or SLL who failed at least one prior treatment regimen will be enrolled in a "3+3" dose escalation and expansion study to determine the Not Tolerated Dose (NTD), the Optimal Biologic Effect dose (OBE) and the Maximum Tolerated Dose (MTD) of Compound 1 and ofatumumab. Approximately 30-42 patients are expected to be enrolled in the study.

Study treatment will be administered in 28-day cycles at specified dose levels as scheduled until disease progression, unacceptable toxicity, or discontinuation for any other reason. Subjects will continue on the starting dose until the preliminary recommended Phase 2 dose (RP2D) is determined, at which point they can be switched to the preliminary RP2D.

Compound 1 besylate and ofatumumab will be administered according to the cohorts for the study, listed in Table 6:

TABLE 6

Study Dosing Schema for Escalating Dose Portion of Study

| COHORT | Compound 1 besylate | Ofatumumab |
|---|---|---|
| 1 | 375 mg BID for days 1-28 | 12 doses administered as follows: 300 mg initial dose, followed 1 week later by 2000 mg weekly for 7 doses, followed 4 weeks later by 2000 mg every 4 weeks for 4 doses |
| 2 | 500 mg BID for days 1-28 | |

Within each cohort, subjects will be treated PO (oral) BID (daily) with Compound 1 besylate according to Table 6 during two initial 28-day treatment cycles and will be assessed for safety, tolerability and DLT, as well as pharmacokinetic ("PK"), pharmacodynamic ("PD"), and disease response.

Ofatumumab will be administered as a single intravenous (IV) infusion. The initial infusion during the first dose will be at a rate of 3.6 mg/hour (12 mL/hour). The infustion rate of dose 2 will be at a rate of 24 mg/hour (12 mL/hour). Subsequent infusion rates will be at 50 mg/hour (25 mL/hour). In the absence of infusional toxicity, the rate of infusion may be increased every 30 minutes as described in Table 7:

TABLE 7

Infusion Rates for Ofatumumab

| Interval After Start of Infusion (min) | Dose 1$^a$ (mL/hour) | Dose 2$^b$ (mL/hour) | Doses 3-12$^b$ (mL/hour) |
|---|---|---|---|
| 0-30 | 12 | 12 | 25 |
| 31-60 | 25 | 25 | 50 |
| 61-90 | 50 | 50 | 100 |
| 91-120 | 100 | 100 | 200 |
| >120 | 200 | 200 | 400 |

$^a$Dose 1 = 300 mg (0.3 mg/mL)
$^b$Doses 2 and 3-12 = 2000 mg (2 mg/mL)

We claim:

1. A method of treating, stabilizing or lessening the severity or progression of a disease or disorder selected from the group consisting of chronic lymphocytic leukemia and small lymphocytic lymphoma in a patient, the method comprising administering to the patient in need thereof therapeutically effective amounts of each of Compound 1, or a pharmaceutically acceptable salt thereof, an anti-CD20 antibody and at least one additional therapeutic agent selected from fludarabine, cyclophosphamide and bendamustine, wherein the therapeutically effective amount of Compound 1 is about 750 mg to about 1000 mg per day, and wherein the patient has failed at least one prior therapy.

2. The method according to claim 1, wherein Compound 1 is administered twice a day.

3. The method according to claim 2, wherein Compound 1 is in the form of a benzenesulfonic acid salt.

4. The method according to claim 3, wherein Compound 1 is administered as an oral dosage form.

5. The method according to claim 3, wherein the anti-CD20 antibody is rituximab.

6. The method according to claim 3, wherein the anti-CD20 antibody is ofatumumab.

7. The method according to claim 5, wherein rituximab is administered once during a 28-day cycle.

8. The method according to claim 7, wherein rituximab is administered as an intravenous infusion.

9. The method according to claim 5, wherein each of Compound 1 and rituximab is administered for at least one 28-day cycle.

10. The method according to claim 1, wherein the therapeutically effective amount of Compound 1 is about 375 mg BID.

11. The method according to claim 1, wherein the therapeutically effective amount Compound 1 is about 500 mg BID.

12. The method according to claim 1, wherein the anti-CD20 antibody is rituximab.

13. The method according to claim 1, wherein the anti-CD20 antibody is ofatumumab.

14. The method according to claim 12, wherein the therapeutically effective amount of rituximab is about 375 mg/m$^2$.

15. The method according to claim 12, wherein the therapeutically effective amount of rituximab is about 500 mg/m$^2$.

16. The method according to claim 1, wherein Compound 1 is administered once a day.

\* \* \* \* \*